US012636109B2

(12) United States Patent (10) Patent No.: US 12,636,109 B2
Xiang et al. (45) Date of Patent: May 26, 2026

(54) MAGNETIC IMPACT NEEDLE ROBOT

(71) Applicant: City University of Hong Kong, Kowloon (HK)

(72) Inventors: Yuxuan Xiang, Kowloon (HK); Jiachen Zhang, Kowloon (HK)

(73) Assignee: City University of Hong Kong, Kowloon (HK)

( * ) Notice: Subject to any disclaimer, the term of this patent is extended or adjusted under 35 U.S.C. 154(b) by 179 days.

(21) Appl. No.: 18/524,268

(22) Filed: Nov. 30, 2023

(65) Prior Publication Data

US 2025/0177073 A1 Jun. 5, 2025

(51) Int. Cl.
*A61B 34/00* (2016.01)
*A61B 34/30* (2016.01)
*A61B 90/11* (2016.01)
*B25J 9/10* (2006.01)

(52) U.S. Cl.
CPC .............. *A61B 34/73* (2016.02); *A61B 34/30* (2016.02); *A61B 90/11* (2016.02); *B25J 9/10* (2013.01)

(58) Field of Classification Search
CPC ... A61B 34/72; A61B 34/73; A61B 2034/731; A61B 5/154123
See application file for complete search history.

(56) References Cited

U.S. PATENT DOCUMENTS

| | | | |
|---|---|---|---|
| 2006/0028751 A1* | 2/2006 | Takeuchi | G02B 26/085 |
| 2010/0069943 A1* | 3/2010 | Roe | A61B 5/15194 |
| | | | 606/181 |
| 2012/0226093 A1* | 9/2012 | Creighton | A61B 17/22012 |
| | | | 977/773 |
| 2013/0154776 A1* | 6/2013 | Mahoney | A61B 34/30 |
| | | | 335/219 |

(Continued)

FOREIGN PATENT DOCUMENTS

WO WO-2018183949 A1 * 10/2018 ....... A61B 17/32053

OTHER PUBLICATIONS

Y. Wang, J. Shen, S. Handschuh-Wang, M. Qiu, S. Du, and B. Wang, "Microrobots for targeted delivery and therapy in digestive system," ACS nano, vol. 17, No. 1, pp. 27-50, 2022.

(Continued)

*Primary Examiner* — Martin T Ton
(74) *Attorney, Agent, or Firm* — Renner, Kenner, Greive, Bobak, Taylor & Weber

(57) ABSTRACT

A tetherless magnetic impact needle robot (MINRob) based on a triple-magnet system with reversible and repeatable magnetic collisions to overcome this constraint on output force. The working procedure of the system is divided into several states, and a mathematical model is developed to predict and optimize the force output. These force values in magnetic impact and penetration are obtained from a customized setup, indicating a 10-fold increase compared with existing miniature robots that only utilize magnetic attrac- (Continued)

tive force. Eventually, the MINRob is integrated with a teleoperation system, enabling remote and precise control of the robot's position and orientation. The triple-magnet system offers promising locomotion patterns and penetration capacity via the notably increased force output, showing great potential in robot-assisted tissue penetration in minimally invasive healthcare.

15 Claims, 24 Drawing Sheets

(56) References Cited

U.S. PATENT DOCUMENTS

| | | | | |
|---|---|---|---|---|
| 2014/0025088 | A1* | 1/2014 | Zarrouk | A61B 34/10 |
| | | | | 606/130 |
| 2019/0290449 | A1* | 9/2019 | Wu | A61B 34/73 |
| 2020/0205793 | A1* | 7/2020 | Jang | A61B 10/0233 |
| 2020/0281670 | A1* | 9/2020 | Moskowitz | A61B 34/30 |
| 2025/0213315 | A1* | 7/2025 | Suzuki | B25J 19/06 |

OTHER PUBLICATIONS

K. E. Peyer, L. Zhang, and B. J. Nelson, "Bio-inspired magnetic swimming microrobots for biomedical applications," Nanoscale, vol. 5, No. 4, pp. 1259-1272, 2013.

B. J. Nelson, I. K. Kaliakatsos, and J. J. Abbott, "Microrobots for minimally invasive medicine," Annual review of biomedical engineering, vol. 12, pp. 55-85, 2010.

T. Gwisai, N. Mirkhani, M. G. Christiansen, T. T. Nguyen, V. Ling, and S. Schuerle, "Magnetic torque-driven living microrobots for increased tumor infiltration," Science Robotics, vol. 7, No. 71, p. eabo0665, 2022.

V. Magdanz, I. S. Khalil, J. Simmchen, G. P. Furtado, S. Mohanty, J. Gebauer, H. Xu, A. Klingner, A. Aziz, M. Medina-Sánchez et al., "Ironsperm: Sperm-templated soft magnetic microrobots," Science ad- vances, vol. 6, No. 28, p. eaba5855, 2020.

J. Yu, D. Jin, K.-F. Chan, Q. Wang, K. Yuan, and L. Zhang, "Active generation and magnetic actuation of microrobotic swarms in bio-fluids," Nature communications, vol. 10, No. 1, p. 5631, 2019.

G. Ciuti, P. Valdastri, A. Menciassi, and P. Dario, "Robotic magnetic steering and locomotion of capsule endoscope for diagnostic and surgical endoluminal procedures," Robotica, vol. 28, No. 2, pp. 199-207, 2010.

X. Yang, W. Shang, H. Lu, Y. Liu, L. Yang, R. Tan, X. Wu, and Y. Shen, "An agglutinate magnetic spray transforms inanimate objects into millirobots for biomedical applications," Science robotics, vol. 5, No. 48, p. eabc8191, 2020.

B. Wang, K. F. Chan, K. Yuan, Q. Wang, X. Xia, L. Yang, H. Ko, Y.-X. J. Wang, J. J. Y. Sung, P. W. Y. Chiu et al., "Endoscopy-assisted magnetic navigation of biohybrid soft microrobots with rapid endoluminal delivery and imaging," Science Robotics, vol. 6, No. 52, p. eabd2813, 2021.

Q. Ze, S. Wu, J. Dai, S. Leanza, G. Ikeda, P. C. Yang, G. Iaccarino, and R. R. Zhao, "Spinning-enabled wireless amphibious origami millirobot," Nature communications, vol. 13, No. 1, p. 3118, 2022.

T. Wang, H. Ugurlu, Y. Yan, M. Li, M. Li, A.-M. Wild, E. Yildiz, M. Schneider, D. Sheehan, W. Hu et al., "Adaptive wireless millirobotic locomotion into distal vasculature," Nature communications, vol. 13, No. 1, pp. 1-17, 2022.

Y. Kim, E. Genevriere, P. Harker, J. Choe, M. Balicki, R. W. Regenhardt, J. E. Vranic, A. A. Dmytriw, A. B. Patel, and X. Zhao, "Telerobotic neu- rovascular interventions with magnetic manipulation," Science Robotics, vol. 7, No. 65, p. eabg9907, 2022.

I. S. Khalil, A. Adel, D. Mahdy, M. M. Micheal, M. Mansour, N. Hamdi, and S. Misra, "Magnetic localization and control of helical robots for clearing superficial blood clots," APL bioengineering, vol. 3, No. 2, 2019.

Y. Xiang and J. Zhang, "A theoretical investigation of the ability of magnetic miniature robots to exert forces and torques for biomedical functionalities," IEEE Robotics and Automation Letters, vol. 8, No. 3, pp. 1771-1777, 2023.

D. Li, M. Jeong, E. Oren, T. Yu, and T. Qiu, "A helical microrobot with an optimized propeller-shape for propulsion in viscoelastic biological media," Robotics, vol. 8, No. 4, p. 87, 2019.

S. Park, B. Ko, H. Lee, and H. So, "Rapid manufacturing of micro-drilling devices using fff-type 3d printing technology," Scientific Reports, vol. 11, No. 1, pp. 1-9, 2021.

M. Li, Y. Tang, R. H. Soon, B. Dong, W. Hu, and M. Sitti, "Miniature coiled artificial muscle for wireless soft medical devices," Science advances, vol. 8, No. 10, p. eabm5616, 2022.

R. H. Soon, Z. Ren, W. Hu, U. Bozuyuk, E. Yildiz, M. Li, and M. Sitti, "On-demand anchoring of wireless soft miniature robots on soft surfaces," Proceedings of the National Academy of Sciences, vol. 119, No. 34, p. e2207767119, 2022.

J. Leclerc, A. Ramakrishnan, N. V. Tsekos, and A. T. Becker, "Magnetic hammer actuation for tissue penetration using a mil-lirobot," IEEE Robotics and Automation Letters, vol. 3, No. 1, pp. 403-410, 2017.

A. Quelin, L. Petit, C. Prelle, and N. Damay, "Experimental performance analysis of an electromagnetic impact-drive microrobot," in 2021 IEEE International Conference on Mechatronics (ICM). IEEE, 2021, pp. 1-6.

J. Zhang, J. Tian, D. Zhu, Y. Liu, and S. Prasad, "Design and experimental investigation of a vibro-impact self-propelled capsule robot with orientation control," in 2022 International Conference on Robotics and Automation (ICRA). IEEE, 2022, pp. 11 381-11 387.

O. Erin, X. Liu, J. Ge, J. Opfermann, Y. Barnoy, L. O. Mair, J. U. Kang, W. Gensheimer, I. N. Weinberg, Y. Diaz-Mercado et al., "Overcoming the force limitations of magnetic robotic surgery: Magnetic pulse actu- ated collisions for tissue-penetrating-needle for tetherless interventions," Advanced Intelligent Systems, p. 2200072, 2022.

W. Li and G. Wang, "Chiral magnetic effects in nuclear collisions," Annual Review of Nuclear and Particle Science, vol. 70, pp. 293-321, 2020.

V. Skokov, A. Y. Illarionov, and V. Toneev, "Estimate of the magnetic field strength in heavy-ion collisions," International Journal of Modern Physics A, vol. 24, No. 31, pp. 5925-5932, 2009.

A. T. Becker, O. Felfoul, and p. E. Dupont, "Toward tissue penetration by mri-powered millirobots using a self-assembled gauss gun," in 2015 IEEE International Conference on Robotics and Automation (ICRA). IEEE, 2015, pp. 1184-1189.

M. von Strauss und Torney, S. Dell-Kuster, H. Hoffmann, U. von Holzen, D. Oertli, and R. Rosenthal, "Microcomplications in laparo-scopic cholecystectomy: impact on duration of surgery and costs," Surgical endoscopy, vol. 30, pp. 2512-2522, 2016.

M. Salehizadeh and E. Diller, "Three-dimensional independent control of multiple magnetic microrobots via inter-agent forces," The Interna- tional Journal of Robotics Research, vol. 39, No. 12, pp. 1377-1396, 2020.

X. Liang, H. Fu, and A. J. Crosby, "Phase-transforming metamaterial with magnetic interactions," Proceedings of the National Academy of Sciences, vol. 119, No. 1, p. e2118161119, 2022.

H. Gu, M. Möckli, C. Ehmke, M. Kim, M. Wieland, S. Moser, C. Bechinger, Q. Boehler, and B. J. Nelson, "Self-folding soft-robotic chains with reconfigurable shapes and functionalities," Nature Communications, vol. 14, No. 1, p. 1263, 2023.

M. P. Kummer, J. J. Abbott, B. E. Kratochvil, R. Borer, A. Sengul, and B. J. Nelson, "Octomag: An electromagnetic system for 5-dof wireless micromanipulation," IEEE Transactions on Robotics, vol. 26, No. 6, pp. 1006-1017, 2010.

W. J. Stronge, Impact mechanics. Cambridge university press, 2018.

A. Costa-Ferreira, p. Rodrigues-Pereira, M. Rebelo, L. O. Vásconez, and J. Amarante, "Morphometric study (macroscopic and microscopic) of the lower abdominal wall," Plastic and Reconstructive Surgery, vol. 134, No. 6, pp. 1313-1322, 2014.

M. Lay, N. L. N. Thajudin, Z. A. A. Hamid, A. Rusli, M. K. Abdullah, and R. K. Shuib, "Comparison of physical and mechanical properties of pla, abs and nylon 6 fabricated using fused

(56) References Cited

OTHER PUBLICATIONS deposition modeling and injection molding," Composites Part B: Engineering, vol. 176, p. 107341, 2019.

M. Dawoud, I. Taha, and S. J. Ebeid, "Mechanical behaviour of abs: An experimental study using fdm and injection moulding techniques," Journal of manufacturing Processes, vol. 21, pp. 39-45, 2016.

A. A. Sharp, A. M. Ortega, D. Restrepo, D. Curran-Everett, and K. Gall, "In vivo penetration mechanics and mechanical properties of mouse brain tissue at micrometer scales," IEEE transactions on biomedical engineering, vol. 56, No. 1, pp. 45-53, 2008.

A. Matthews, C. Hutnik, K. Hill, T. Newson, T. Chan, and G. Campbell, "Indentation and needle insertion properties of the human eye," Eye, vol. 28, No. 7, pp. 880-887, 2014.

K. Owen, N. Blackie, and T. J. Gibson, "The effect of needle reuse on piglet skin puncture force," Veterinary Sciences, vol. 9, No. 2, p. 90, 2022.

M. Khadem, C. Rossa, R. S. Sloboda, N. Usmani, and M. Tavakoli, "Mechanics of tissue cutting during needle insertion in biological tissue," IEEE Robotics and Automation Letters, vol. 1, No. 2, pp. 800-807, 2016.

O. Onaizah and E. Diller, "Tetherless mobile micro-surgical scissors using magnetic actuation," in 2019 International Conference on Robotics and Automation (ICRA). IEEE, 2019, pp. 894-899.

C. Forbrigger, A. Lim, O. Onaizah, S. Salmanipour, T. Looi, J. Drake, and E. D. Diller, "Cable-less, magnetically driven forceps for minimally invasive surgery," IEEE Robotics and Automation Letters, vol. 4, No. 2, pp. 1202-1207, 2019.

D. Son, H. Gilbert, and M. Sitti, "Magnetically actuated soft capsule endoscope for fine-needle biopsy," Soft robotics, vol. 7, No. 1, pp. 10-21, 2020.

Jake J. Abbott, Eric Diller, and Andrew J. Petruska, "Magnetic Methods in Robotics," Annu. Rev. Control Robot. Auton. Syst. 2020. 3:57-90.

* cited by examiner

MAGNETIC IMPACT NEEDLE ROBOT

FIELD OF INVENTION

This invention relates to magnetic small-scale robots, e.g., for biomedical applications.

BACKGROUND OF INVENTION

Magnetic small-scale robots exhibit significant potentials to be employed in demanding scenarios in biomedical applications [1]-[3] with various functionalities [4]-[7]. These robots can achieve non-invasive access and remote navigation in hard-to-reach regions buried deep inside human bodies (e.g., gastrointestinal tract [8]-[10], blood vessel [11]-[13]). To attain these functionalities, magnetic field actuators induce magnetic force and torque to the robot body, which function as an end-effector to conduct desired tasks. However, demanding real-world biomedical functionalities (e.g., long-lasting anchoring and tissue penetration) can hardly be accomplished, attributed to insufficient force and torque output [14]. The values of output forces and torques decrease exponentially with decreasing robot size and increasing actuating distance.

Previous studies have demonstrated various tailored robot structures to enhance the mechanical output [15], [16]. However, these designs fail to essentially increase the magnetic interaction force. Considering the restrictions of present peripherals, pure magnetic pulling force and torque exerted on small-scale robots rarely fulfill the requirements of targeted mechanical operations in real-world biomedical applications (e.g., tissue penetration and removal) [14]. Researchers generate potentially larger force and torque output via extra energy to resolve these challenges. For example, elastic potential energy pre-stored through deformable elastomers has been adopted with unique elastic properties [17] and spring structures [18]. Nevertheless, an additional energy source is often required to trigger the energy release. Meantime, such pre-deformed structures are one-offs and thus are not applicable for continuous outputs and operations sustained over a long period of time.

On the other hand, kinetic energy resulting from pulse-induced momentum offers an alternative solution to generate instantaneous and enormous magnetic force. This approach has been applied to a millirobot composed of a free-to-move spherical magnet inside a hollow tubular shell [19], where the magnetic pulse generated by a pair of electromagnetic coils actuates the spherical magnet to accelerate along the tube. The momentary impact amplifies the force when the high-speed sphere hits the rigid plate on the anterior side. The direction of the magnetic pulse is switched with a frequency up to several hertzes to accomplish reversible forward and backward locomotion of the sphere. In addition, magnetic impact systems with two [20], [21] and three degree-of-freedoms (DOFs) [22] have been developed to extend the locomotion of the robots, enabling them to navigate in unstructured environments, such as interior cavities, ducts, and vessels of the human body. Although such collisions between magnetic parts and non-magnetic parts are reversible, the pulse-based impact demands a significantly high frequency with substantial energy density. Meanwhile, a spacious gap is required to fully accelerate the robot before impact, which is incompatible with the inherently limited onboard space of small-scale robots.

The magnetic field-induced collision between multiple magnetic parts is demonstrated to increase energy intensity in limited space. It is commonly observed in nuclear physics at the micro-level [23]. Examples include the chiral magnetic effect (CME) for the heavy-ion collision [24]. Nonetheless, there are few applications of collision between multiple magnetized components at the macro-level. A Gauss gun triggered by a magnetic resonance imaging (MRI) scanner can induce collisions between spherical permanent magnets and steel spheres [25]. Apart from the global force externally applied by the magnetic field, the additional local attractive force increases exponentially as one magnetized component approaches an-other. Such momentum-induced inelastic collisions propagate along the approaching direction to the robot body. However, the firing of the Gauss gun is disposable and irreversible due to the immense attractive force of magnetic coupling, failing to meet the requirements for continuous and repeated operations in biomedical applications [26].

Meanwhile, the aforementioned designs are confined by the field generators in surgical environments, such as electromagnetic coil systems and clinical MRI scanners. These electromagnetic coil systems also require preprogrammed signals and bulky cooling modules to accomplish sophisticated and high-frequency switching. Furthermore, commercial sintered permanent magnets (e.g., neodymium iron boron, or NdFeB) are extremely brittle materials with high operational risk, and thus magnetic collision can damage materials and cause physical injury during operations.

REFERENCES

The following references are referred to throughout this specification, as indicated by the numbered brackets:

[1] Y. Wang, J. Shen, S. Handschuh-Wang, M. Qiu, S. Du, and B. Wang, "Microrobots for targeted delivery and therapy in digestive system," ACS nano, vol. 17, no. 1, pp. 27-50, 2022.

[2] K. E. Peyer, L. Zhang, and B. J. Nelson, "Bio-inspired magnetic swimming microrobots for biomedical applications," Nanoscale, vol. 5, no. 4, pp. 1259-1272, 2013.

[3] B. J. Nelson, I. K. Kaliakatsos, and J. J. Abbott, "Microrobots for minimally invasive medicine," Annual review of biomedical engineering, vol. 12, pp. 55-85, 2010.

[4] T. Gwisai, N. Mirkhani, M. G. Christiansen, T. T. Nguyen, V. Ling, and S. Schuerle, "Magnetic torque-driven living microrobots for increased tumor infiltration," Science Robotics, vol. 7, no. 71, p. eabo0665, 2022.

[5] V. Magdanz, I. S. Khalil, J. Simmchen, G. P. Furtado, S. Mohanty, J. Gebauer, H. Xu, A. Klingner, A. Aziz, M. Medina-Sa nchez et al., "Ironsperm: Sperm-templated soft magnetic microrobots," Science advances, vol. 6, no. 28, p. eaba5855, 2020.

[6] J. Yu, D. Jin, K. F. Chan, Q. Wang, K. Yuan, and L. Zhang, "Active generation and magnetic actuation of microrobotic swarms in bio-fluids," Nature communications, vol. 10, no. 1, p. 5631, 2019.

[7] G. Ciuti, P. Valdastri, A. Menciassi, and P. Dario, "Robotic magnetic steering and locomotion of capsule endoscope for diagnostic and surgical endoluminal procedures," Robotica, vol. 28, no. 2, pp. 199-207, 2010.

[8] X. Yang, W. Shang, H. Lu, Y. Liu, L. Yang, R. Tan, X. Wu, and Y. Shen, "An agglutinate magnetic spray transforms inanimate objects into millirobots for biomedical applications," Science robotics, vol. 5, no. 48, p. eabc8191, 2020.

[9] B. Wang, K. F. Chan, K. Yuan, Q. Wang, X. Xia, L. Yang, H. Ko, Y.-X. J. Wang, J. J. Y. Sung, P. W. Y. Chiu et al., "Endoscopy-assisted magnetic navigation of biohybrid soft microrobots with rapid endoluminal delivery and imaging," Science Robotics, vol. 6, no. 52, p. eabd2813, 2021.

[10] Q. Ze, S. Wu, J. Dai, S. Leanza, G. Ikeda, P. C. Yang, G. Iaccarino, and R. R. Zhao, "Spinning-enabled wireless amphibious origami millirobot," Nature communications, vol. 13, no. 1, p. 3118, 2022.

[11] T. Wang, H. Ugurlu, Y. Yan, M. Li, M. Li, A.-M. Wild, E. Yildiz, M. Schneider, D. Sheehan, W. Hu et al., "Adaptive wireless millirobotic locomotion into distal vasculature," Nature communications, vol. 13, no. 1, pp. 1-17, 2022.

[12] Y. Kim, E. Genevriere, P. Harker, J. Choe, M. Balicki, R. W. Regenhardt, J. E. Vranic, A. A. Dmytriw, A. B. Patel, and X. Zhao, "Telerobotic neurovascular interventions with magnetic manipulation," Science Robotics, vol. 7, no. 65, p. eabg9907, 2022.

[13] I. S. Khalil, A. Adel, D. Mahdy, M. M. Micheal, M. Mansour, N. Hamdi, and S. Misra, "Magnetic localization and control of helical robots for clearing superficial blood clots," APL bioengineering, vol. 3, no. 2, 2019.

[14] Y. Xiang and J. Zhang, "A theoretical investigation of the ability of magnetic miniature robots to exert forces and torques for biomedical functionalities," IEEE Robotics and Automation Letters, vol. 8, no. 3, pp. 1771-1777, 2023.

[15] D. Li, M. Jeong, E. Oren, T. Yu, and T. Qiu, "A helical microrobot with an optimized propeller-shape for propulsion in viscoelastic biological media," Robotics, vol. 8, no. 4, p. 87, 2019.

[16] S. Park, B. Ko, H. Lee, and H. So, "Rapid manufacturing of micro-drilling devices using fff-type 3d printing technology," Scientific Reports, vol. 11, no. 1, pp. 1-9, 2021.

[17] M. Li, Y. Tang, R. H. Soon, B. Dong, W. Hu, and M. Sitti, "Miniature coiled artificial muscle for wireless soft medical devices," Science advances, vol. 8, no. 10, p. eabm5616, 2022.

[18] R. H. Soon, Z. Ren, W. Hu, U. Bozuyuk, E. Yildiz, M. Li, and M. Sitti, "On-demand anchoring of wireless soft miniature robots on soft surfaces," Proceedings of the National Academy of Sciences, vol. 119, no. 34, p. e2207767119, 2022.

[19] J. Leclerc, A. Ramakrishnan, N. V. Tsekos, and A. T. Becker, "Magnetic hammer actuation for tissue penetration using a millirobot," IEEE Robotics and Automation Letters, vol. 3, no. 1, pp. 403-410, 2017.

[20] A. Quelin, L. Petit, C. Prelle, and N. Damay, "Experimentalperformance analysis of an electromagnetic impact-drive microrobot," in 2021 IEEE International Conference on Mechatronics (ICM). IEEE, 2021, pp. 1-6.

[21] J. Zhang, J. Tian, D. Zhu, Y. Liu, and S. Prasad, "Design and experimental investigation of a vibro-impact self-propelled capsule robot with orientation control," in 2022 International Conference on Robotics and Automation (ICRA). IEEE, 2022, pp. 11 381-11 387.

[22] O. Erin, X. Liu, J. Ge, J. Opfermann, Y. Barnoy, L. O. Mair, J. U. Kang, W. Gensheimer, I. N. Weinberg, Y. Diaz-Mercado et al., "Overcoming the force limitations of magnetic robotic surgery: Magnetic pulse actuated collisions for tissue-penetrating-needle for tetherless interventions," Advanced Intelligent Systems, p. 2200072, 2022.

[23] W. Li and G. Wang, "Chiral magnetic effects in nuclear collisions," Annual Review of Nuclear and Particle Science, vol. 70, pp. 293-321, 2020.

[24] V. Skokov, A. Y. Illarionov, and V. Toneev, "Estimate of the magnetic field strength in heavy-ion collisions," International Journal of Modern Physics A, vol. 24, no. 31, pp. 5925-5932, 2009.

[25] A. T. Becker, O. Felfoul, and P. E. Dupont, "Toward tissue penetration by mri-powered millirobots using a self-assembled gauss gun," in 2015 IEEE International Conference on Robotics and Automation (ICRA). IEEE, 2015, pp. 1184-1189.

[26] M. von Strauss und Torney, S. Dell-Kuster, H. Hoffmann, U. von Holzen, D. Oertli, and R. Rosenthal, "Microcomplications in laparo-scopic cholecystectomy: impact on duration of surgery and costs," Surgical endoscopy, vol. 30, pp. 2512-2522, 2016.

[27] M. Salehizadeh and E. Diller, "Three-dimensional independent control of multiple magnetic microrobots via inter-agent forces," The International Journal of Robotics Research, vol. 39, no. 12, pp. 1377-1396, 2020.

[28] X. Liang, H. Fu, and A. J. Crosby, "Phase-transforming metamaterial with magnetic interactions," Proceedings of the National Academy of Sciences, vol. 119, no. 1, p. e2118161119, 2022.

[29] H. Gu, M. Möckli, C. Ehmke, M. Kim, M. Wieland, S. Moser, C. Bechinger, Q. Boehler, and B. J. Nelson, "Self-folding soft-robotic chains with reconfigurable shapes and functionalities," Nature Communications, vol. 14, no. 1, p. 1263, 2023.

[30] M. P. Kummer, J. J. Abbott, B. E. Kratochvil, R. Borer, A. Sengul, and B. J. Nelson, "Octomag: An electromagnetic system for 5-dof wireless micromanipulation," IEEE Transactions on Robotics, vol. 26, no. 6, pp. 1006-1017, 2010.

[31] W. J. Stronge, Impact mechanics. Cambridge university press, 2018.

[32] A. Costa-Ferreira, P. Rodrigues-Pereira, M. Rebelo, L. O. Va sconez, and J. Amarante, "Morphometric study (macroscopic and microscopic) of the lower abdominal wall," Plastic and Reconstructive Surgery, vol. 134, no. 6, pp. 1313-1322, 2014.

[33] M. Lay, N. L. N. Thajudin, Z. A. A. Hamid, A. Rusli, M. K. Abdullah, and R. K. Shuib, "Comparison of physical and mechanical properties of pla, abs and nylon 6 fabricated using fused deposition modeling and injection molding," Composites Part B: Engineering, vol. 176, p. 107341, 2019.

[34] M. Dawoud, I. Taha, and S. J. Ebeid, "Mechanical behaviour of abs: An experimental study using fdm and injection moulding techniques," Journal of manufacturing Processes, vol. 21, pp. 39-45, 2016.

[35] A. A. Sharp, A. M. Ortega, D. Restrepo, D. Curran-Everett, and K. Gall, "In vivo penetration mechanics and mechanical properties of mouse brain tissue at micrometer scales," IEEE transactions on biomedical engineering, vol. 56, no. 1, pp. 45-53, 2008.

[36] A. Matthews, C. Hutnik, K. Hill, T. Newson, T. Chan, and G. Campbell, "Indentation and needle insertion properties of the human eye," Eye, vol. 28, no. 7, pp. 880-887, 2014.

[37] K. Owen, N. Blackie, and T. J. Gibson, "The effect of needle reuse on piglet skin puncture force," Veterinary Sciences, vol. 9, no. 2, p. 90, 2022.

[38] M. Khadem, C. Rossa, R. S. Sloboda, N. Usmani, and M. Tavakoli, "Mechanics of tissue cutting during needle insertion in biological tissue," IEEE Robotics and Automation Letters, vol. 1, no. 2, pp. 800-807, 2016.

[39] O. Onaizah and E. Diller, "Tetherless mobile micro-surgical scissors using magnetic actuation," in 2019 International Conference on Robotics and Automation (ICRA). IEEE, 2019, pp. 894-899.

[40] C. Forbrigger, A. Lim, O. Onaizah, S. Salmanipour, T. Looi, J. Drake, and E. D. Diller, "Cable-less, magnetically driven forceps for minimally invasive surgery," IEEE Robotics and Automation Letters, vol. 4, no. 2, pp. 1202-1207, 2019.

[41] D. Son, H. Gilbert, and M. Sitti, "Magnetically actuated soft capsule endoscope for fine-needle biopsy," Soft robotics, vol. 7, no. 1, pp. 10-21, 2020.

SUMMARY OF INVENTION

Accordingly, the present invention, in one aspect, is a magnet impact device, which includes an impacting portion comprising a first permanent magnet and a second permanent magnet, and a third permanent magnet external to the impacting portion. The third permanent magnet is adapted to actuate the impacting portion to perform a striking action along a linear direction.

In some embodiments, both of the first and second permanent magnets are spherical magnets.

In some embodiments, the impacting portion further contains a casing defining an inner chamber, in which the first and second permanent magnets are received. The second permanent magnet is adapted to translate within the inner chamber.

In some embodiments, the first permanent magnet is adapted to rotate only.

In some embodiments, the third permanent magnet is adapted to rotate, resulting in synchronized rotations of the first and second permanent magnets.

In some embodiments, the impacting portion undergoes a complete striking cycle when the third permanent magnet undergoes an actuating cycle as it rotates.

In some embodiments, the actuating cycle of the third permanent magnet is 180° of rotation.

In some embodiments, during the complete striking cycle the second permanent magnet is repelled from the first permanent magnet and then bounces back, resulting in the striking action of the impacting portion.

In some embodiments, the third permanent magnet is a cubic permanent magnet.

In some embodiments, the impacting portion of the magnet impact device is a magnetic impact needle robot, and the impacting portion further comprises a needle coupled to the impacting portion.

According to another aspect of the invention, there is provided a small-scale robotic system, which includes a magnet impact device as mentioned above, a first robotic arm to which a camera or an ultrasonic probe is installed, and a second robotic arm to which the third permanent magnet and a motor are installed. The motor is coupled with the third permanent magnet and is adapted to drive the third permanent magnet of the magnet impact device to rotate.

One can see that embodiments of the invention provide magnet impact devices with triple-magnet systems, which are able to achieve repeatable collision at various speeds, leading to a notably larger force output from the millirobot compared with preceding studies. A macro-scale magnetic collision that is reversible is introduced, and the robotic system is integrated with a computer-aided teleoperation platform. There is demonstrated promising locomotion patterns and great potentials in robot-assisted tissue penetration in minimally invasive healthcare.

The foregoing summary is neither intended to define the invention of the application, which is measured by the claims, nor is it intended to be limiting as to the scope of the invention in any way.

BRIEF DESCRIPTION OF FIGURES

The foregoing and further features of the present invention will be apparent from the following description of embodiments which are provided by way of example only in connection with the accompanying figures, of which:

FIG. 5b is a graph that shows a simulation of the angle differences $|\theta_1-\theta_2|$ varying with $\theta_0$, for the magnetic components of FIG. 5a.

FIG. 5c is a graph that shows magnetic forces exerted by PM0 and PM2 on PM1 which vary with $\theta$, for the magnetic components of FIG. 5a.

FIG. 5d shows a critical bouncing-off state of the triple-magnet system when PM1 bounces off for a maximum distance $\Delta r_{max}$, for the magnetic components of FIG. 5a.

FIG. 5e shows an ideal orientation of the triple-magnet system when PM1 hits back, where all the magnetic dipole moments are aligned along the X-axis, for the magnetic components of FIG. 5a.

FIG. 6b are 2D distribution maps illustrating the impact force with varying diameters of PM1 and PM2 for the triple-magnet system of FIG. 6a.

FIG. 6c shows achievable impact forces of different PM0 for the triple-magnet system of FIG. 6a.

FIG. 6d shows achievable actuating distance ranges of the different PM0 for the triple-magnet system of FIG. 6a.

Figure 7:
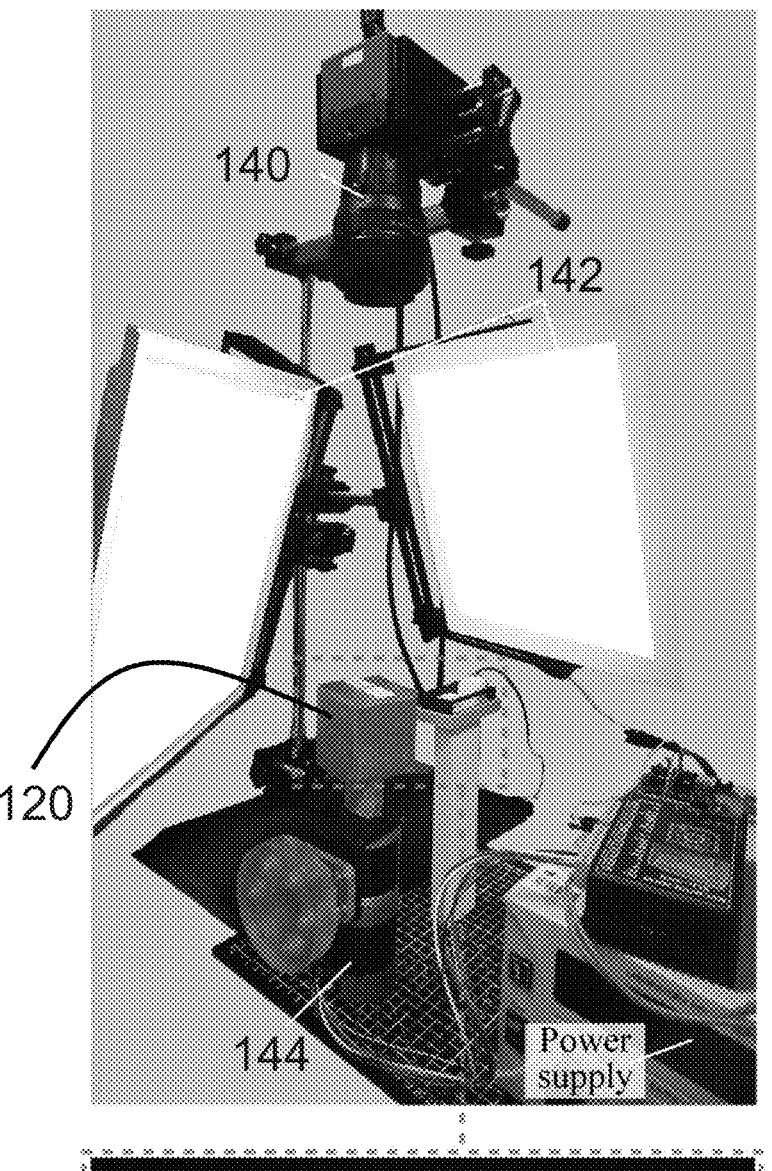
FIG. 7 is an image showing an experimental setup of the evaluation of the impact process of the magnetic impact needle robot of FIG. 2.
Figure 7:
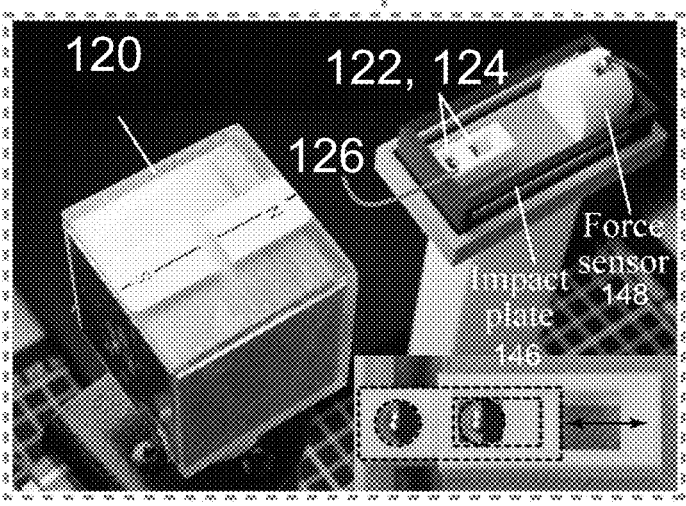

with varying rotation frequency of the actuating permanent magnet PM0, for the experimental setup of FIG. 7.

Figures 9A, 9B:
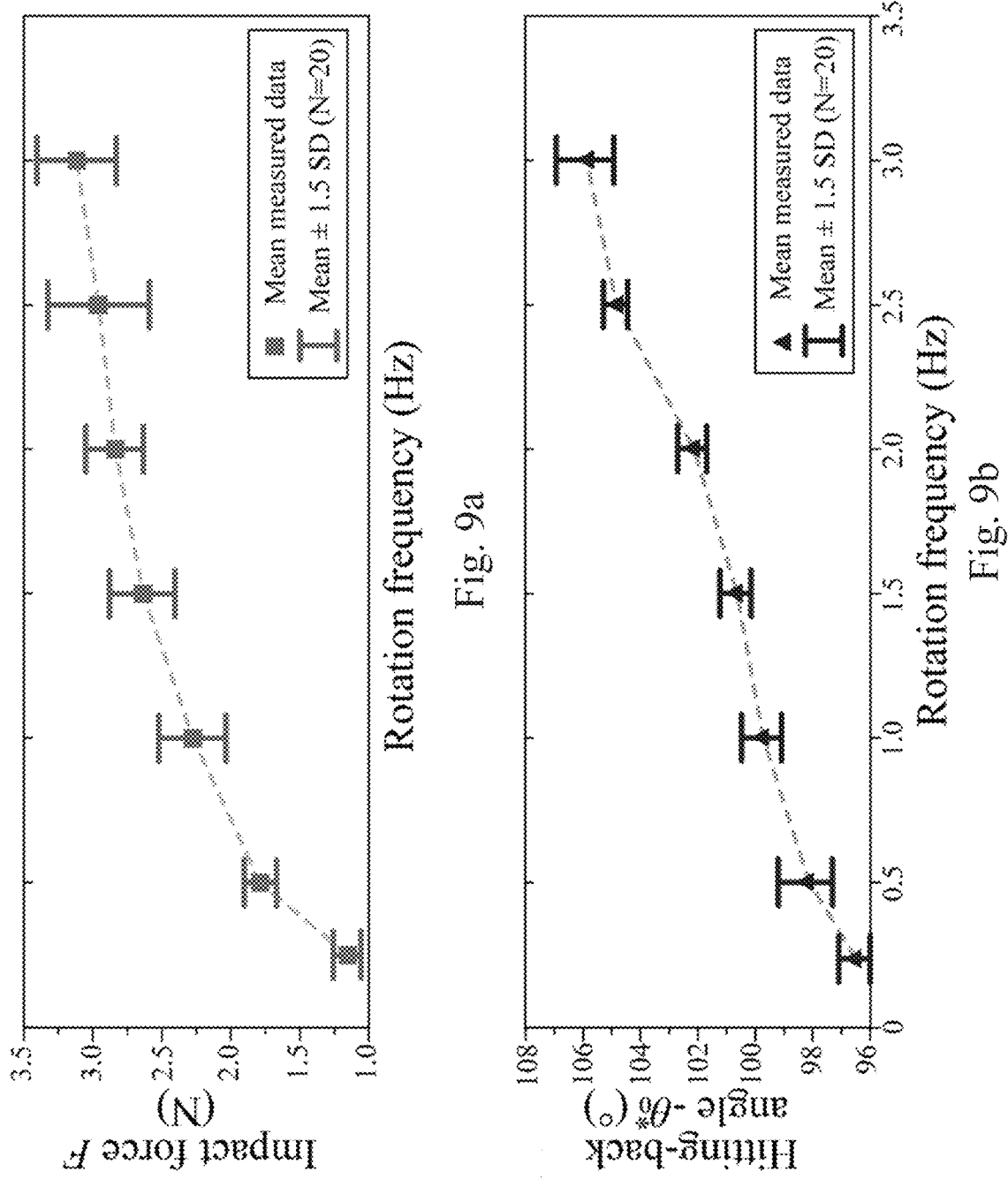
FIG. 9*a* shows measured impact force F with varying rotation frequency of the actuating permanent magnet PM0, for the experimental setup of FIG. 7.
FIG. 9*b* shows hitting-back angle $$\theta_0^*$$
Figure 9C:
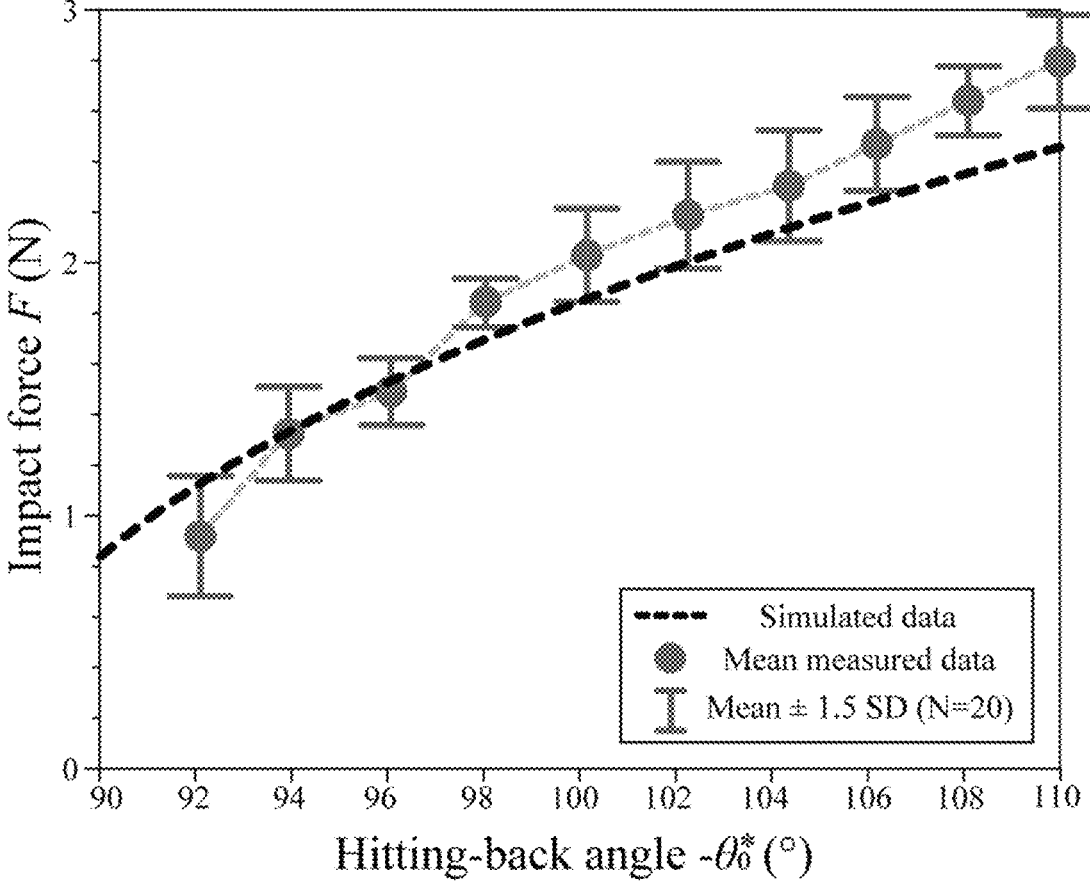

FIG. 9*c* illustrates impact force F with varying hitting-back angle PM0 of the actuating permanent magnet PM0, for which experimental data are compared with the simulated data, for the experimental setup of FIG. 7.

Figure 10:
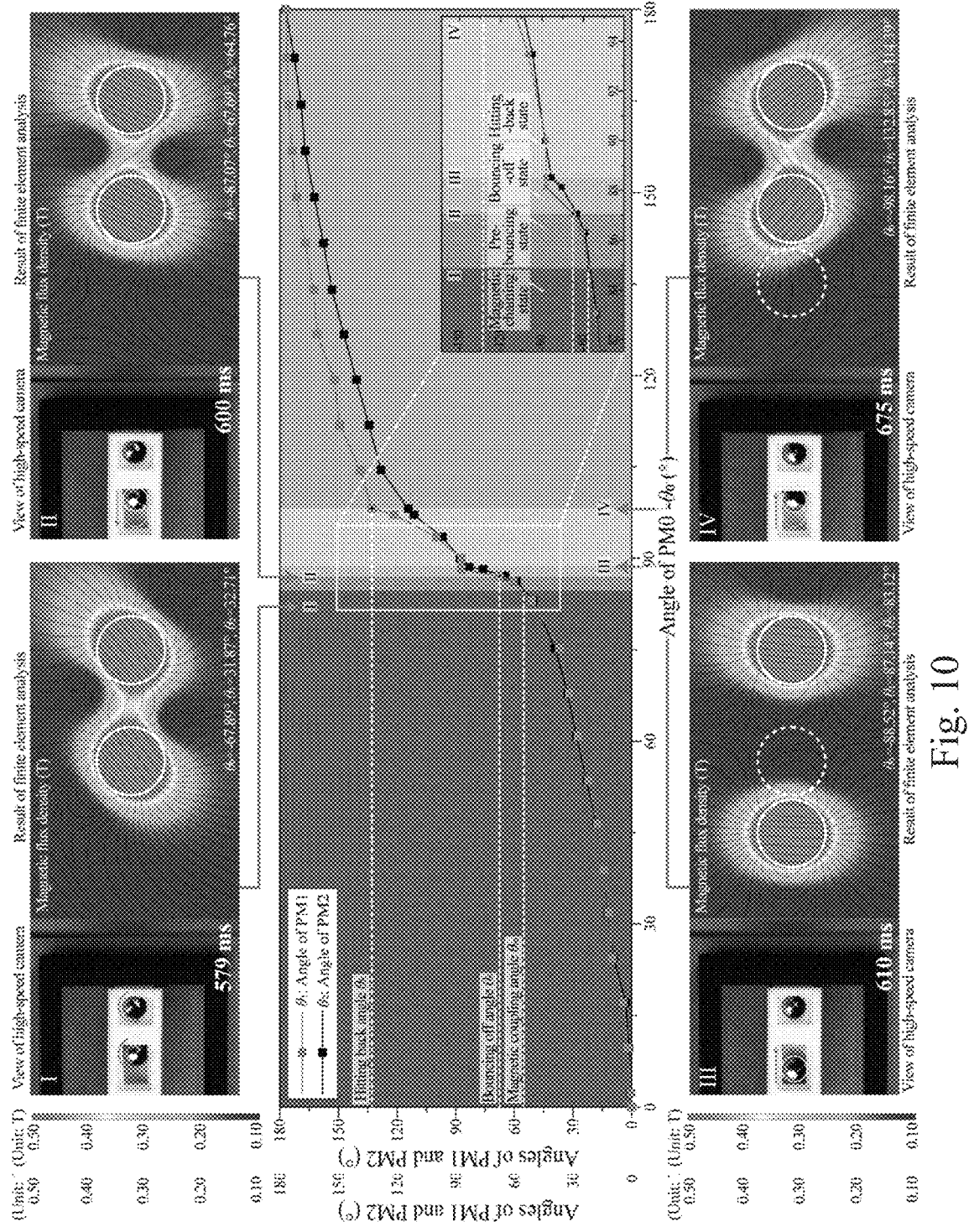

FIG. 10 illustrates representative curves illustrating angle variations of PM1 and PM2, and snapshots of the specific transitional states are listed together with corresponding FEA results illustrating the magnetic flux density distribution, for the experimental setup of FIG. 7.

Figure 11:
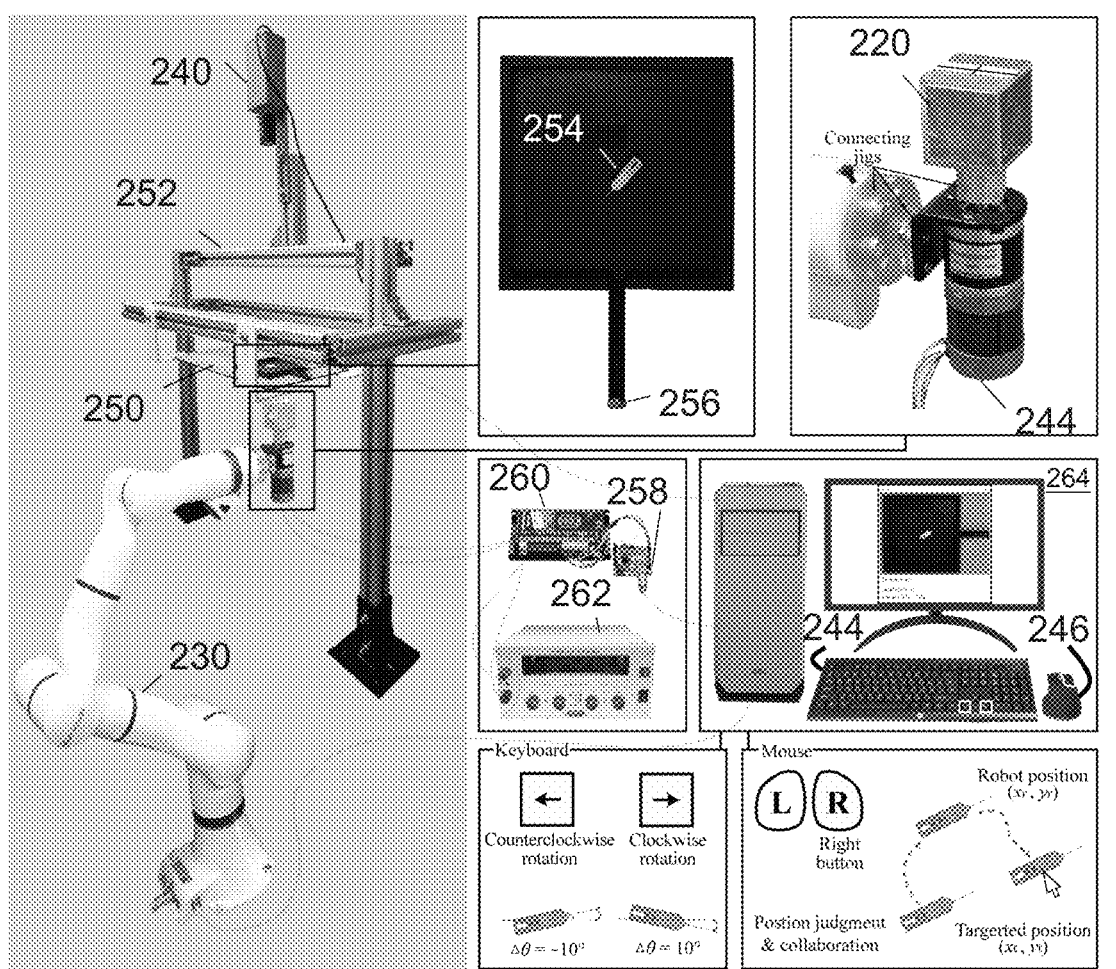

FIG. 11 is a schematic diagram illustrating a teleoperation robotic system including a workbench and a MINRob, according to another embodiment of the invention.

Figure 12A:
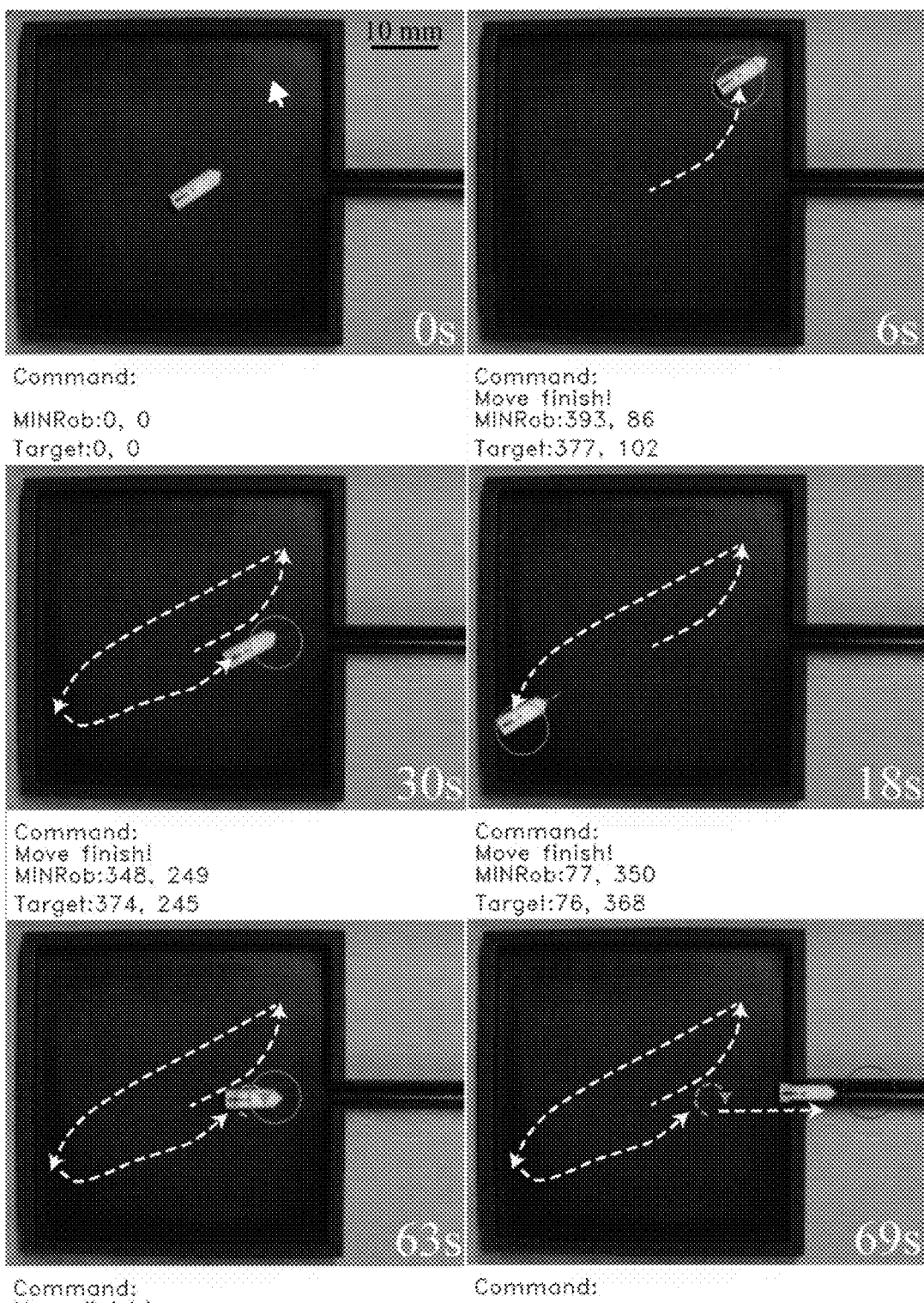

FIG. 12*a* illustrates the planar locomotions of the MIN-Rob integrated with the teleoperation robotic system.

Figure 12B:
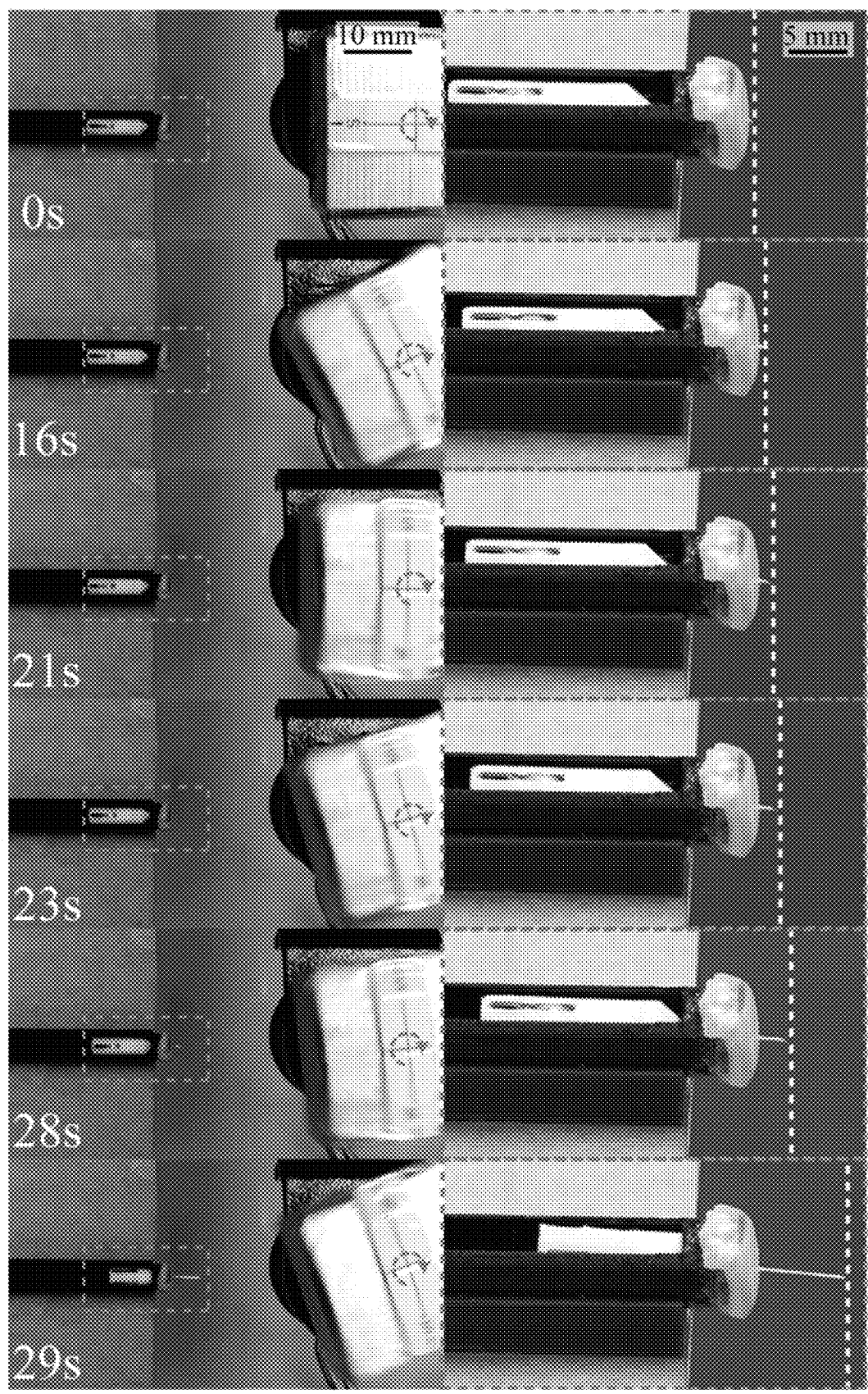

FIG. 12*b* illustrates penetration performance of the MIN-Rob to puncture a multi-layer film.

Figure 12C:
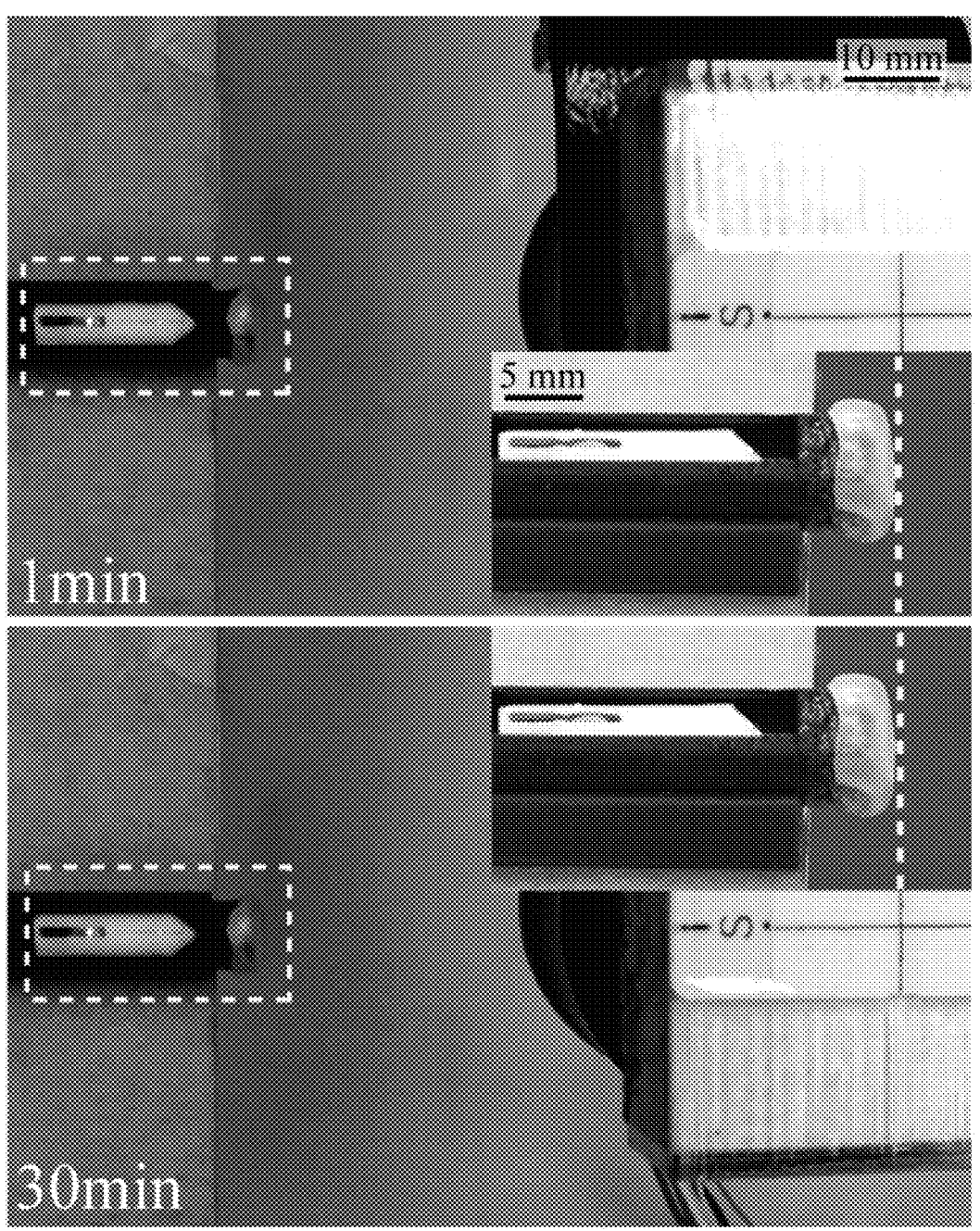

FIG. 12*c* shows a control group for the penetration performance of the MINRob.

Figure 12D:
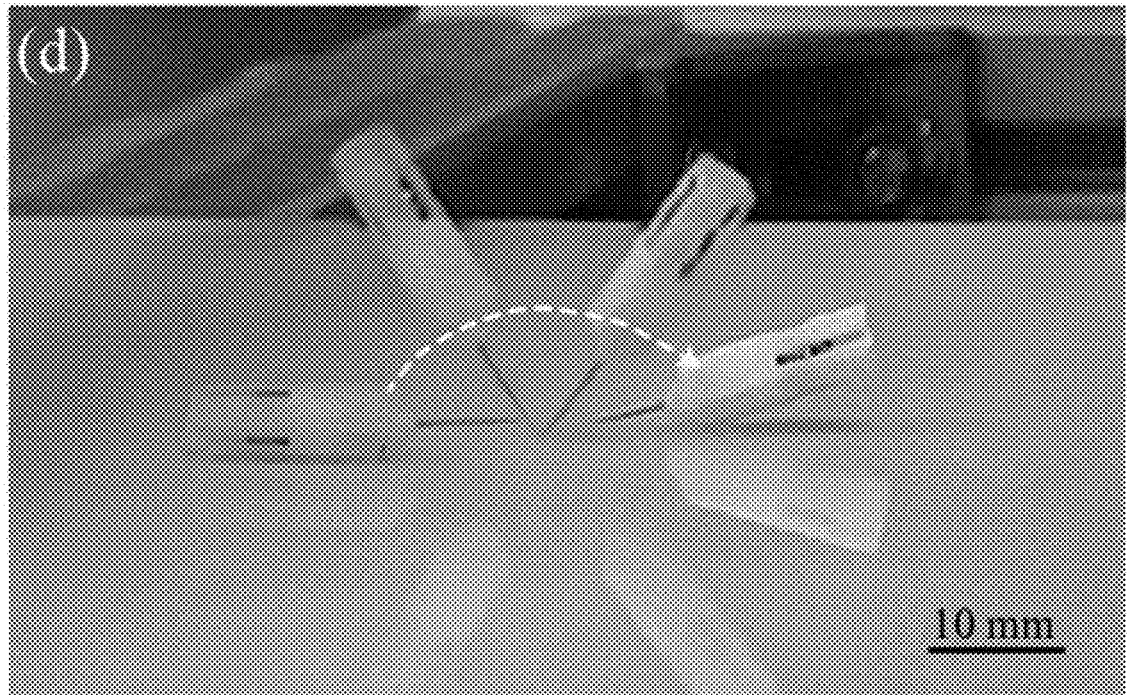

FIG. 12*d* illustrates a 3D rolling motion of the MINRob.

Figure 13:
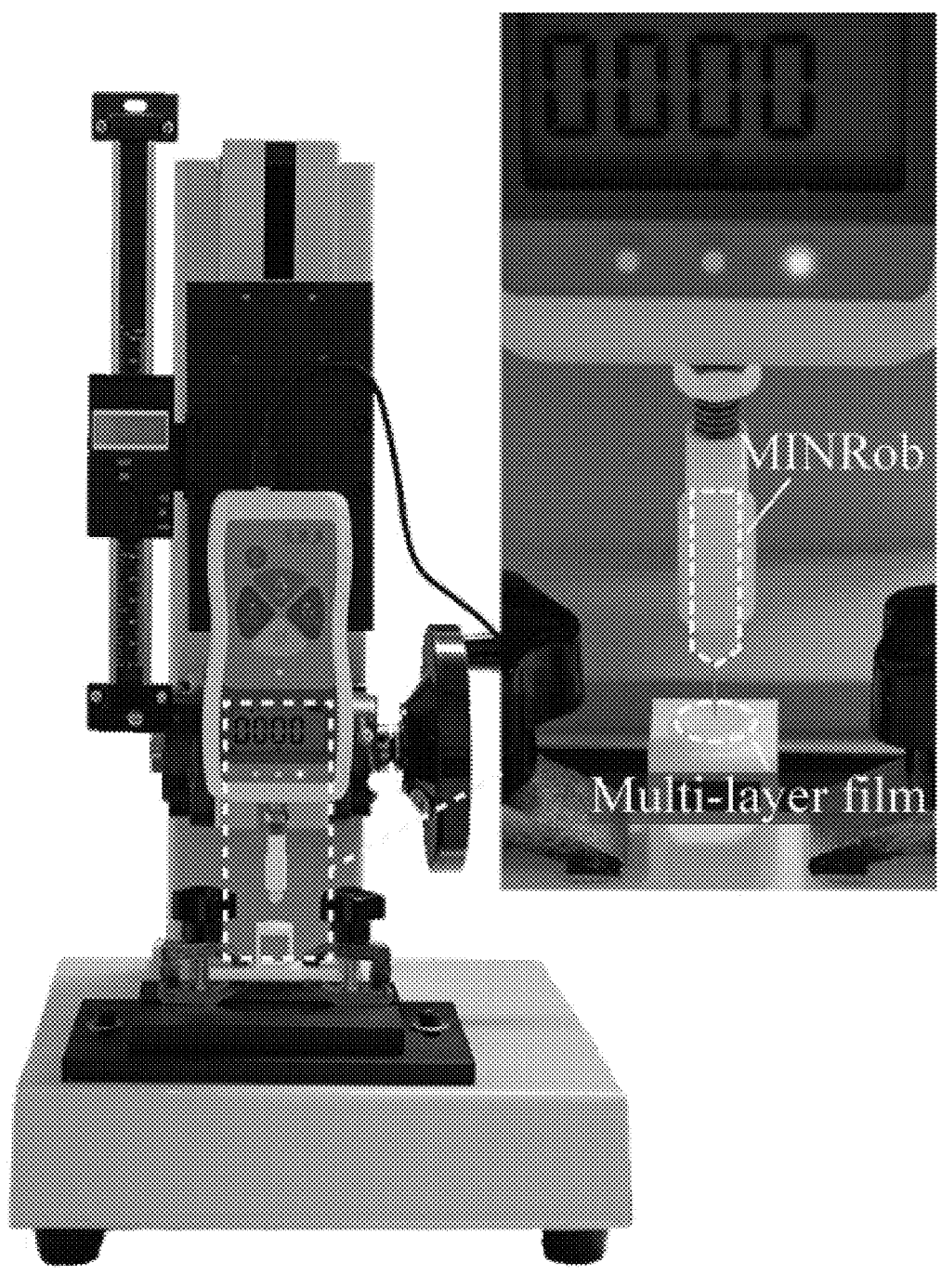

FIG. 13 illustrates an experimental setup mimicking the impact process of a MINRob according to another embodiment of the invention.

Figure 14A:
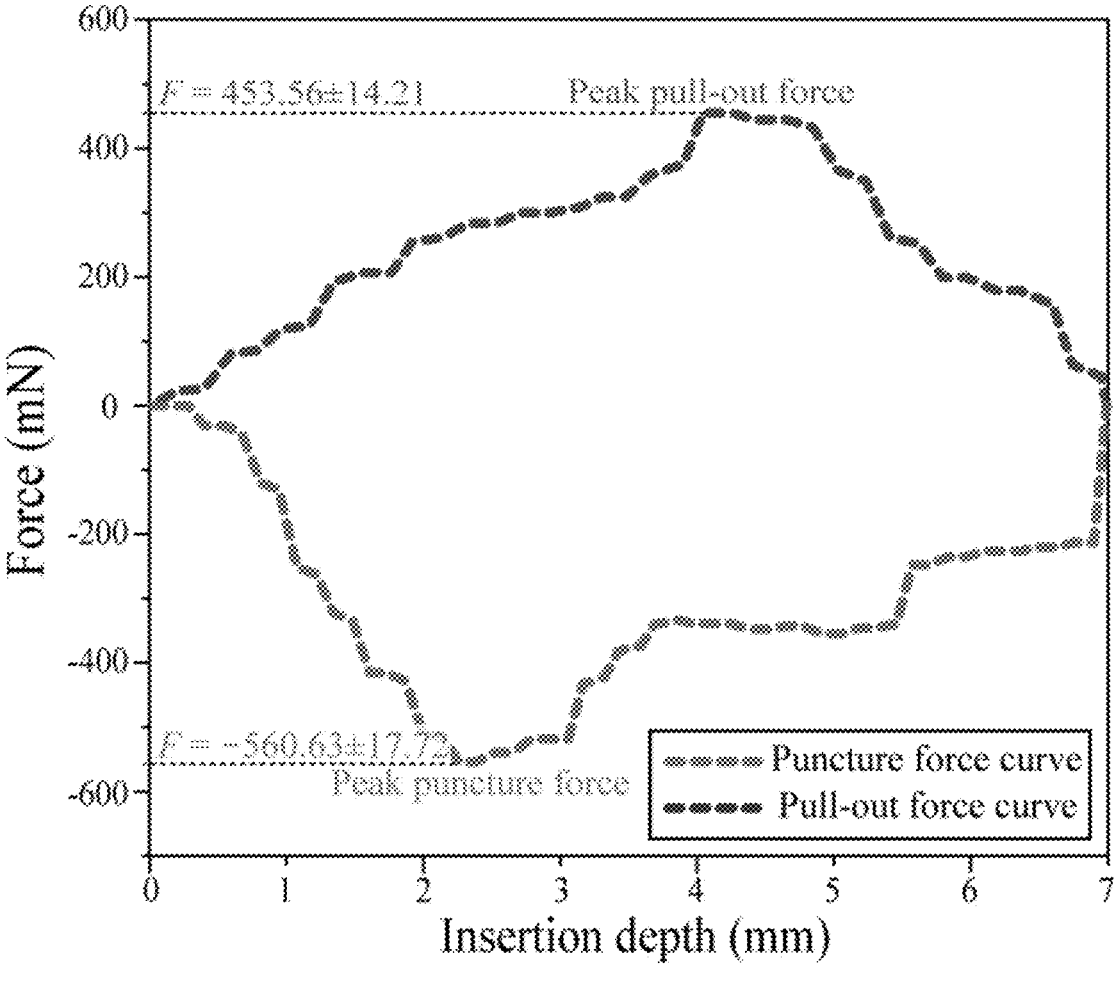

FIG. 14*a* shows representative curves of both puncture and pull-out forces vary with the insertion depth measured in the experiment.

Figure 14B:
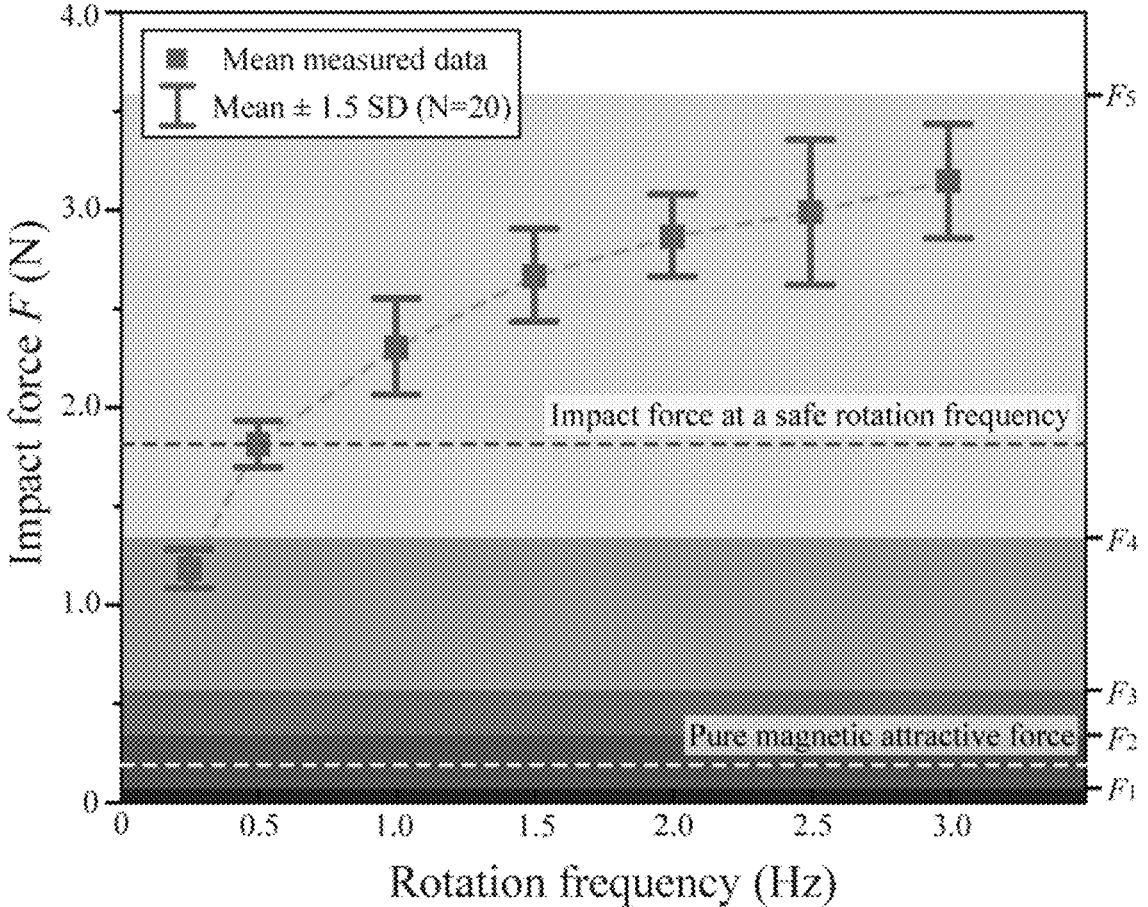

FIG. 14*b* shows a comparison of the force value between the triple-magnet system and specific application scenarios.

In the drawings, like numerals indicate like parts throughout the several embodiments described herein.

DETAILED DESCRIPTION

Figure 1:
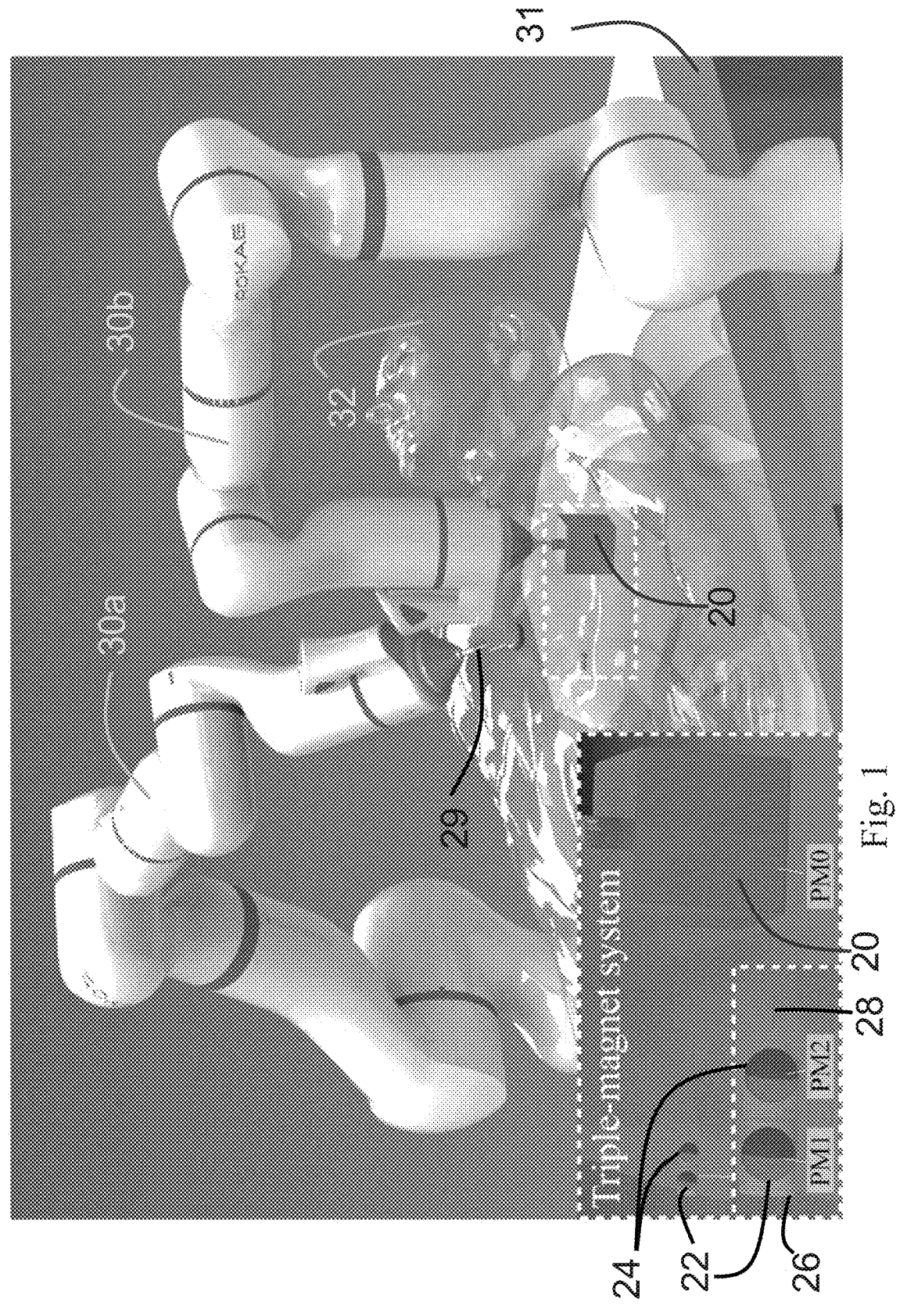
FIG. 1 is a three-dimensional illustration of a small-scale robotic system according to a first embodiment of the invention, the inserts showing the triple-magnet system of the magnet impact device in the system.
Figure 2:
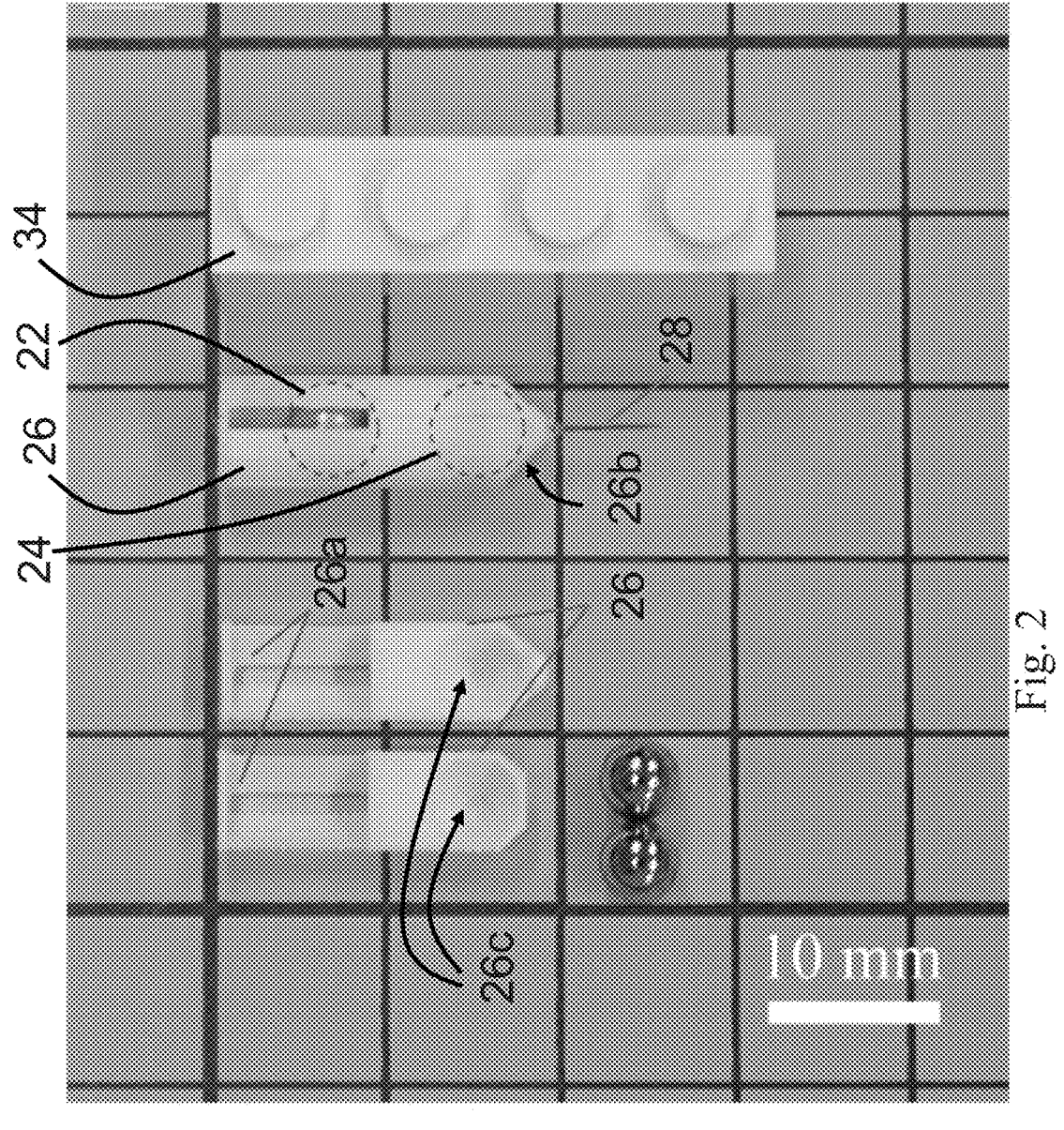
FIG. 2 shows a photograph of a magnetic impact needle robot (MINRob) in the magnet impact device of FIG. 1, with both an assembled view and a partial view of the magnetic impact needle robot.

Referring now to FIGS. 1 and 2, a first embodiment of the invention is a small-scale robotic system which includes a first robotic arm 30*a* and a second robotic arm 30*b*, with an ultrasonic probe 29 connected to a free end of the first robotic arm 30*a*, and a third permanent magnet 20 connected to a free end of a second robotic arm 30*b*. In FIG. 1, an exemplary scenario is demonstrated where a patient 32 is laying on a table 31, and the small-scale robotic system which is teleoperated (e.g., by a computer, which is not shown) allows a magnetic robot of the magnet impact device to be deployed inside the human body of the patient 32 for minimally invasive diagnostic or therapeutic applications. The magnetic robot is not connected to either of the first and second robotic arms 30*a*, 30*b*. As such, the robot is fully untethered and is only controlled by a magnetic field generated by the third permanent magnet 20 wirelessly, but there is no cable connection or any mechanical connection to the robot. The magnetic robot for example may be deployed inside the human body of the patient 32 in advance to any operation. The magnetic robot is a MINRob, and is part of a triple-magnet system, the structure and working principle of which will be described in detail below. The triple-magnet system is able to achieve repeatable collision at various speeds, leading to a notably larger force output from the magnetic robot (also called a millirobot herein) compared to conventional art. Within the magnetic robot, macro-scale magnetic collision is achieved.

The first and second robotic arms 30*a*, 30*b* each have a seven degrees-of-freedom (DOFs), and for the sake of brevity the structure of the first and second robotic arms 30*a*, 30*b* and their working principles will not be described in detail here, which are known to those skilled in the art. On the free end of the first robotic arm 30*a*, the ultrasonic probe 29 is installed as an end effector to provide visual information of the magnetic robot. On the other hand, on the free end of the second robotic arm 30*b*, the third magnet 20 is installed as an end effector of the second robotic arm 30*b*. The third magnet 20 is adapted to rotate as driven by a motor (not shown) installed on the second robotic arm 30*b*, and is also denoted by PM0 in this description.

Inserts of FIG. 1 as well as FIG. 2 show the internal structure of the magnetic robot, which contains a casing 26 that defines an impacting portion of the magnetic robot, a first magnet 22, and a second magnet 24. The casing 26 may be fabricated by polylactic acid (PLA) via 3D printing (for example Raise3D Pro3 Plus). In one implementation, the casing 26 is divided into two halves that can be glued together to position the first magnet 22 and the second magnet 24 therein. The first magnet 22 and the second magnet 24 are both spherical magnets (the physical appearances of which are shown in FIG. 2), and are also denoted by PM1 and PM2 respectively in this description. The casing 26 has a substantially cylindrical shape, in which an inner chamber is defined. However, one end of the casing 26 is formed with a conical portion 26*b* (best shown in FIG. 2), at the tip of which a needle 28 is installed. The third magnet 20 is external to the casing 26, and has a cubic shape. The third magnet 20 does not physically contact the casing 26. All of the first magnet 22, the second magnet 24, and the third magnet 20 are permanent magnets. The magnetic robot has a needle 28 as the working member of the robot. The needle 28 for example can be a clinical needle 25G supplied by Kindly Medical Inc. The needle 28 is able to utilize the induced large impact force for potential medical applications (e.g., tissue penetration), while minimizing the undesired swinging motion of the robot.

The first magnet 22 and the second magnet 24 are located within the casing 26, but are movable with respect to the casing 26. In particular, the first magnet 22 which is located farther to the needle 28 and the third magnet 20 is adapted to rotate and translate within the casing 26. On the other hand, the second magnet 24 which is located closer to the needle 28 and the third magnet 20 is adapted to rotate only and is unable to translate. The third magnet 20 is an actuating permanent magnet, the second magnet 24 is an active permanent magnet, and the first magnet 22 is a passive permanent magnet. The casing 26 acts as a container for the first magnet 22 and the second magnet 24, so as to achieve a locomotion of the first magnet 22. As shown in FIG. 2, the casing 26 is formed with a spherical cavity 26*c* for accommodating the first magnet 22, and an elongated cavity 26*a* is formed within the casing 26 for the second magnet 24 to be received and move linearly in the elongated cavity 26*a*. The elongated cavity 26*a* and the spherical cavity 26*c* together define an internal chamber of the casing 26. It should be noted that the first magnet 22 and the second magnet 24 are not in direct contact at any time, although their magnetic fields interfere with each other. As shown in FIG. 2, the length of the casing 26 (excluding the needle 28) is only a little bit more than half the length of a 1×4 Lego™ brick 34.

Figure 3:
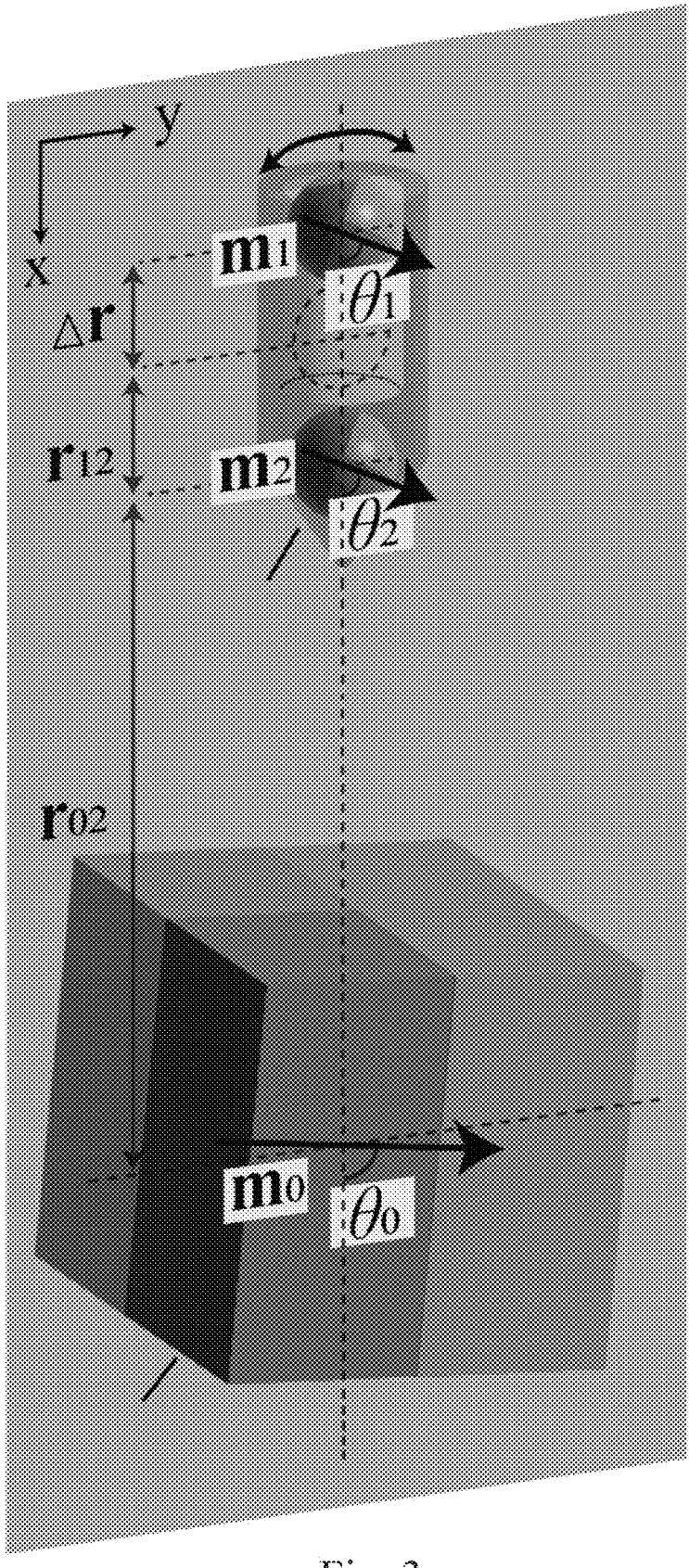
FIG. 3 shows a schematic diagram of the magnetic interactions and actuating process of the magnetic impact needle robot of FIGS. 1-2, with relevant variables defined in the developed mathematical model.

Turning to FIG. 3, in which a schematic diagram is provided to illustrate the magnetic interactions and actuating process of the triple-magnet system of FIG. 1 with relevant variables defined in the developed mathematical model. The mathematical model developed for the system in various states is applied for the X-Y plane, as shown in FIG. 3. The corresponding magnetic moments of PM0, PM1, and PM2 are denoted as $m_0 \in R^{3 \times 1}$, $m_1 \in R^{3 \times 1}$, and $m_2 \in R^{3 \times 1}$. PM0 has its position, rotating frequency, and rotating direction are actively controlled by a teleoperation system. As mentioned above, PM1 is free to rotate and translate within the inner chamber, while sphere PM2 can only rotate.

Figure 4:
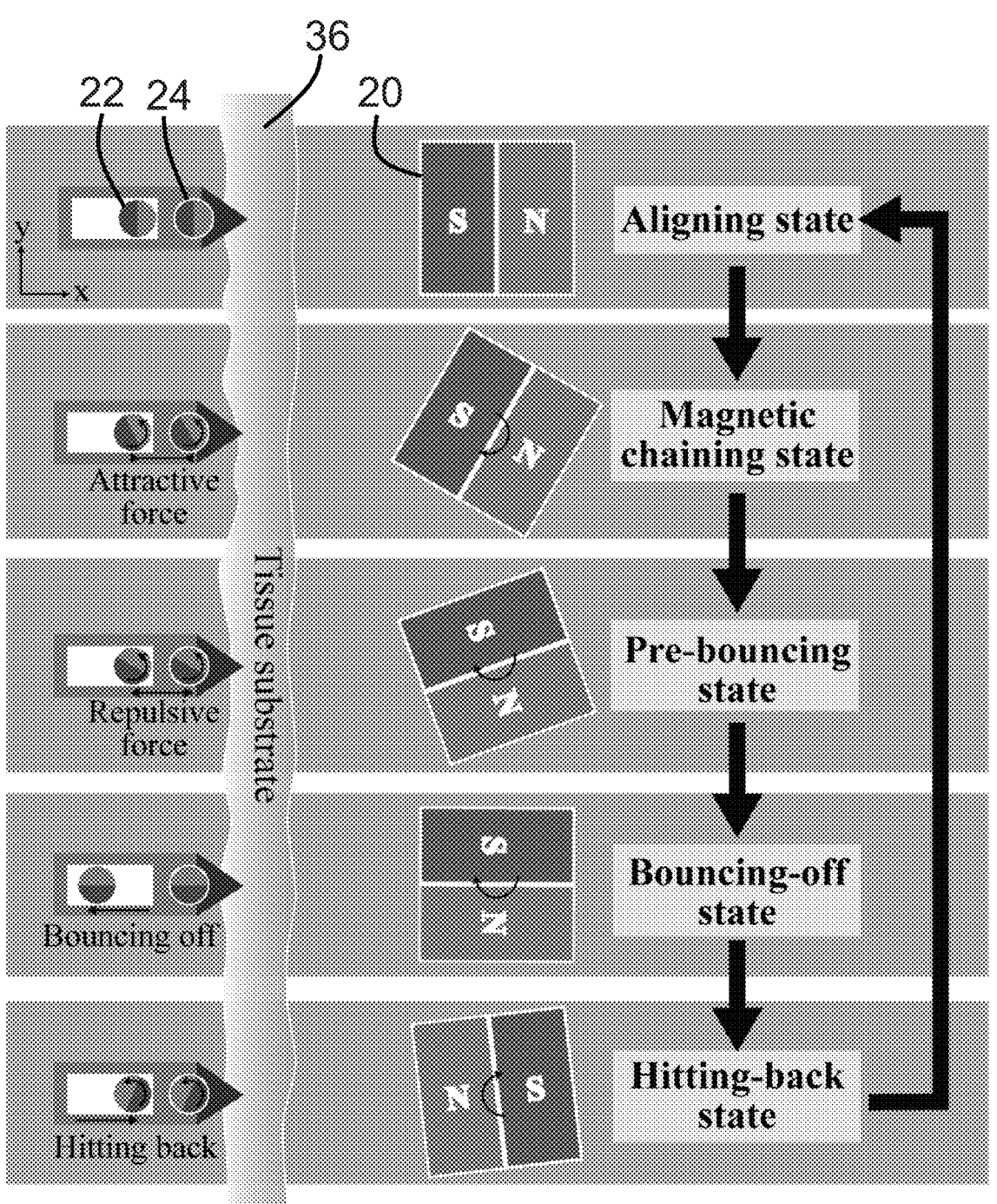
FIG. 4 shows the orientation and position of individual magnetic components in various states, during a striking cycle of an impacting portion of the magnetic impact needle robot of FIG. 3.

FIG. 4 shows the orientation and position of individual magnetic components in five different states. The magnetic robot is illustrated to continually hit and insert into a tissue substrate 36 under the actuation of the third magnet 20. The orientations of PM1 (i.e., the first magnet 22) and PM2 (i.e., the second magnet 24) are determined by PM0 (i.e. the third magnet 20), of which the magnetic moment aligns with PM1 and PM2 at the initial aligning state and rotates to induce the magnetic chaining, bouncing-off, and hitting-back state (see FIG. 4). The one-dimensional (1D) impact system can be easily applied to any direction in the 3D space by manipulating PM0. It is noted that the displacement and force components in the Z-axis are zero due to the automatic magnetic alignment of the work planes.

An ideal orientation of the impact along the X-axis is discussed in this model. In real-world applications, the robot composed of PM1 and PM2 tends to swing in the X-Y plane simultaneously due to the magnetic torque induced by the rotating PM0. This undesired swinging motion can be mitigated by spatial constraints in a hollow tube, the tip-needle anchoring, or by increasing the actuating distance of PM0.

In an ideal configuration, PM1 and PM2 rotate synchronously with the rotating PM0. As the rotation angle exceeds a threshold, the local magnetic attractive force between PM1 and PM2 converts into repulsive force, as presented in "Pre-bouncing state" in FIG. 4, which induces a "bouncing-off" motion of the free-to-translate sphere PM1. A significantly large impact force is induced when PM1 hits back.

Previous research has studied the interaction forces between two magnetic agents in a uniform external magnetic field [27]-[29]. But the model shown in FIGS. 3-4 provides a more generic investigation of two magnetic agents (i.e., PM1 and PM2) in a non-uniform magnetic field. By considering both force and torque interactions, it is more applicable to real-world healthcare scenarios.

Figure 5A:
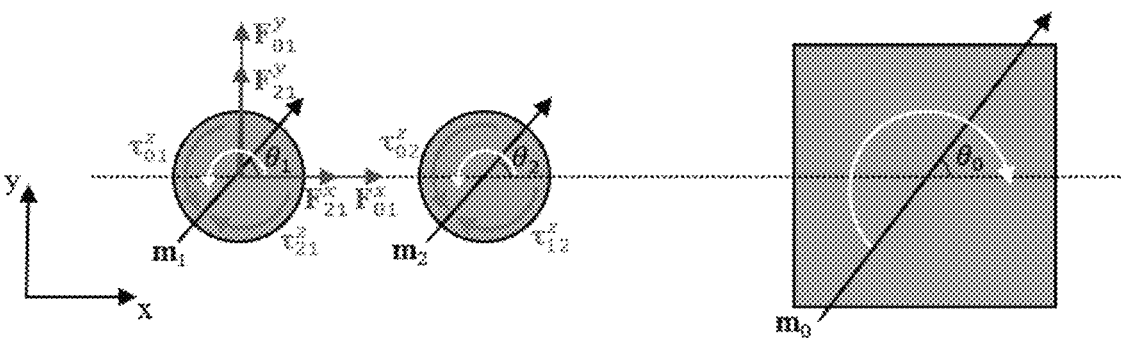
FIG. 5a illustrates angular transformations, positions, and orientations of the magnetic components in the magnetic impact needle robot of FIG. 3, including basic parameters involved in the mathematical model of the triple-magnet system.

As shown in FIG. 5a, a clockwise rotation of PM0 leads to counterclockwise rotations of both PM1 and PM2. Thus, the rotating angle of PM0, PM1, and PM2 are denoted as $\theta_0 \in (-2\pi, 0]$, $\theta_1 \in [0, 2\pi)$, and $\theta_2 \in [0, 2\pi)$. For $i \in \{0, 1, 2\}$, then:

$$m_i = [m_i \cos\theta_i, m_i \sin\theta_i, 0]^T \tag{1}$$

where $m_i$ is the numerical value of the corresponding magnetic dipole moment, and the distance vector between the magnetic dipole moment center of PM0 and PM2, PM1 and PM2 are denoted as $r_{02} \in R^{3 \times 1}$ and $r_{12} \in R^{3 \times 1}$, respectively. The magnetic flux density $B_j$ at a point $P_j \in R^{3 \times 1}$ (for $j \in \{0, 1, 2\}$) generated by $m_i$ at point $P_j \in R^{3 \times 1}$ is calculated as $$B_i(P_j) = \frac{\mu_0}{4\pi r_{ij}^3}\left(3\hat{r}_{ij}\hat{r}_{ij}^T - \mathbb{1}_3\right)m_i \tag{2}$$

where $\mu_0 = 4\pi \times 10^{-7}$ H/m is the vacuum permeability, $r_{ij}$ is the distance vector from $m_j$ dipole center $P_i$ to point $P_j$, $\hat{r}_{ij}$ is the unit vector in this direction, $r_{ij}$ is the distance length, and $\mathbb{1}^3$ is the 3×3 identity matrix. The magnetic force $F_{ij} \in R^{3 \times 1}$ and torque $t_{ij} \in R^{3 \times 1}$ of $m_j$ at point $P_j$ generated by $m_i$ are calculated as $$F_{ij}(P_j) = \frac{3\mu_0}{4\pi r_{ij}^4}\left(\left(\hat{r}_{ij}^T m_i\right)m_j + \left(\hat{r}_{ij}^T m_j\right)m_i + \left(m_i^T m_j - 5\left(\hat{r}_{ij}^T m_i\right)\left(\hat{r}_{ij}^T m_j\right)\right)\hat{r}_{ij}\right) \tag{3}$$

$$\tau_{ij}(P_j) = m_j \times B_i(P_j) \tag{4}$$

A. Aligning State

In the initial aligning state, the magnetic moment directions of PM0, PM1, and PM2 are aligned along the X-axis, as illustrated in "Aligning state" in FIG. 4. One can see that both PM1 and PM2 have their north poles facing the south pole of PM0. In this specific state, $\theta_1$ and $\theta_2$ can be calculated from (5) due to the torque equilibrium on PM1 and PM2 as PM0 rotates for a degree $\theta_0$.

$$\begin{cases} \tau_{21}^z(P_1) = -\tau_{01}^z(P_1) \\ \tau_{12}^z(P_2) = -\tau_{02}^z(P_2) \end{cases} \tag{5}$$

Figure 5B:
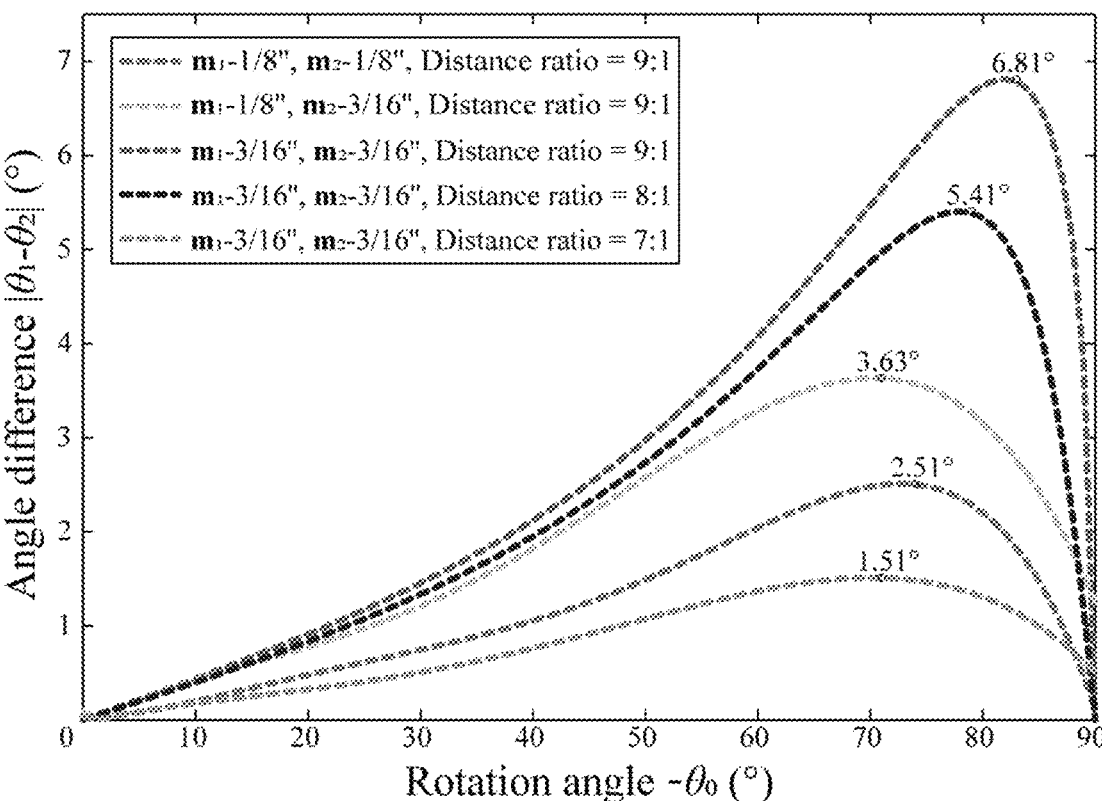

Different sizes of commercial permanent magnets for PM0, PM1 and PM2 are considered, and the actuating distance ratios $\alpha_r = r_{02}/r_{12}$ is varied. The angle difference between $\theta_1$ and $\theta_2$ is shown in FIG. 5b, which grows non-monotonically with $\theta_0$. For the simulation in FIG. 5b, the cubic magnet PM0 has a sidelength of 2 inches and a magnetic moment of 140.317 Am². The simulated data of magnetic components are collected from commercial NdFeB magnets (K&J Inc.). The model indicates that the angle difference is small, which can be reduced to ~1.5° by controlling $m_1$, $m_2$, and $\alpha_r$. Meanwhile, the actual angle difference can be further reduced by frictions, which is validated by experimental data that will be described later. Thus, it is assumed that $\theta_1 = \theta_2$ as $\theta_0$ varies, denoted as $\theta$ to represent the rotation of PM1 and PM2. As $\theta_0$ of rotating PM0 varies from 0 to $-2\pi$, $\theta$ increases from 0 to $2\pi$, and an angle $\theta = \theta_b \in [0, \pi/2)$ is expected when PM1 begins to bounce off, which are valid for both aligning state and magnetic chaining state as $\theta < \theta_b$.

B. Magnetic Chaining State

The magnetic forces and torques follow $\propto$ $$\propto r_{ij}^{-4} \text{ and } \propto r_{ij}^{-3}$$

based on (2) (3) (4), respectively. Thus, the local magnetic interaction between PM1 and PM2 is supposed to be strong due to the relatively small $r_{12}$. It can accomplish an even stronger global magnetic interaction by controlling $m_0$ and $r_{02}$ with PM0. In this case, PM1 and PM2 are attractive to each other attributed to the local interaction. They rotate synchronously due to the global interaction generated by PM0, referred to as magnetic chaining, which is presented in "Magnetic Chaining State" in FIG. 4. In particular, PM0 rotates clockwise, and as a result both PM1 and PM2 rotate counterclockwise.

The torque between PM0 and PM2 mainly determines the angle θ, given the one between PM0 and PM1 is much weaker. The global torque $$\tau_{02}^z$$

must overcome the internal torque $$\tau_{12}^z$$

between PM2 and PM1 to ensure synchronized rotation. Based on (4), the internal torque is:

$$\tau_{12}^z = -\frac{3\mu_0 m_1 m_2}{8\pi r_{12}^3}\sin 2\theta \qquad (6)$$

To investigate the minimum magnetic torque required to lift PM1 and PM2 from the magnetic chaining state, a critical condition is considered, where the magnetic torque $$\tau_{02}^z(\theta_0, \theta)$$

(θ₀, θ) is the function of both θ₀ and θ. It is observed from the experiments that $$\theta_0 \sim -\frac{\pi}{2}$$

where a maximum torque $$\tau_{02max}^z$$

is:

$$\tau_{02max}^z = -\frac{\mu_0 m_0 m_2}{4\pi r_{02}^3}\cos\theta \qquad (7)$$

An ideal orientation of the impact along the X-axis is discussed in this model. In real-world applications, the robot composed of PM1 and PM2 tends to swing in the X-Y plane simultaneously due to the magnetic torque induced by the rotating PM0. This undesired swinging motion can be mitigated by spatial constraints in a hollow tube, the tip-needle anchoring, or by increasing the actuating distance of PM0.

Thus, to ensure the rotation of PM1 and PM2 in the chaining state, it is required that |

$$|\tau_{02max}^z| \geq |\tau_{12}^z|,$$

which demands:

$$\alpha_r \leq \left(\frac{m_0}{3m_1}\right)^{\frac{1}{3}} \qquad (8)$$

Based on (3), the force exerted by PM2 to PM1 in the X-axis is calculated as:

$$F_{21}^x = \frac{3\mu_0 m_1 m_2}{4\pi r_{12}^4}\left(2\cos^2\theta - \sin^2\theta\right) \qquad (9)$$

Figures 5C, 5D, 5E:
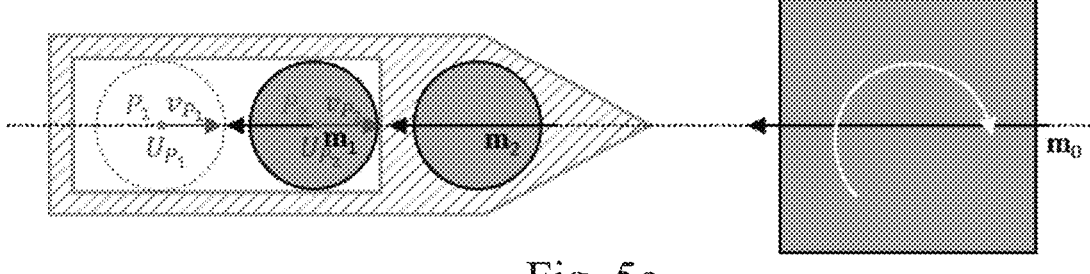

Under a rotating magnetic field exerted by PM0, PM1 and PM2 can rotate simultaneously for the same degree θ. As θ increases up to a critical angle $$\theta_m = 54.74°, F_{21}^x$$

changes from attractive force to repulsive force as shown in FIG. 5c, which drives the system into the pre-bouncing state.

C. Pre-Bouncing State

Due to the global magnetic interaction between PM1 and PM0, the additional attractive force $$F_{01}^x$$

exerted by PM0 to PM1 prevents PM1 from bouncing off immediately. As PM1 and PM2 rotate to θ_m=54.74°, PM1 is yet to be bounced off, as illustrated in "Pre-bouncing state" in FIG. 4. The force $$F_{01}^x(\theta_0, \theta)$$

(θ₀, θ) is maximized with $$\theta_0 = \frac{\pi}{2},$$

and thus $$F_{01max}^x$$

is calculated by (10):

$$F_{01max}^x = -\frac{3\mu_0 m_1 m_2}{4\pi(r_{12}+r_{02})^4}\sin\theta \qquad (10)$$

The forces $$F_{01max}^x \text{ and } F_{21}^x$$

with respect to the chaining angle θ are plotted in FIG. 5c, and the total force $$F_{21}^x + F_{01max}^x$$

applied to PM1 is calculated. The internal force between PM1 and PM2 changes from attractive to repulsive as $\theta$ increases, while the global force between PM1 and PM0 remains to be attractive and increases with $\theta$. When PM1 is ready to bounce off, it is required that the total force is repulsive. Thus, by solving $$F_{21}^x + F_{01max}^x = 0,$$

=0, the lower limit of the distance ratio $\alpha_r$ is obtained:

$$\alpha_r \geq \left(\frac{m_0}{m_2}\right)^{\frac{1}{4}} - 1 \tag{11}$$

D. Bouncing-Off State

PM1 bounces off along the X direction as the actuating distance ratios $\alpha_r$ fall between the ranges determined by (8) and (11). The corresponding maximum bouncing-off distance of PM1 is denoted as $\Delta r_{max}$. An ideal state with maximum bouncing-off distance is shown in FIG. 5d, where all magnetic moments of the triple-magnet system align with the Y-axis. Such a configuration is further verified by experiments. Based on the ideal configuration at point $P_1$, $\Delta r_{max}$ is calculated via the force balance $$F_{01max}^x(P_1) = -F_{21}^x(P_1):$$

$$\Delta r_{max} = -\frac{r_{02}\left(\frac{m_2}{m_0}\right)^{\frac{1}{4}}}{\left(\frac{m_2}{m_0}\right)^{\frac{1}{4}} - 1} - r_{12} \tag{12}$$

E. Hitting-Back State

As PM0 continues to rotate clockwise, PM1 hits back to the initial position $P_2$ after achieving the maximum bouncing-off distance $\Delta r_{max}$. An ideal alignment of the triple-magnet system with maximum impact velocity is illustrated in FIG. 5e where all the magnetic moments align along the X-axis. During the hitting-back process, the velocity of PM1 at point $P_1$ is $v_{P1}=0$, and the velocity $v_{P2}$ at point $P_2$ is calculated based on the conservation of energy:

$$U_{P_1} - U_{P_2} = \frac{1}{2}\overline{m}v_{P_2}^2 \tag{13}$$

where $\overline{m}$ is the mass of PM1, $U_{Pj}$ is the magnetic potential energy of PM1 at point $P_j$, which is calculated by:

$$U_{P_j} = -m_1 \cdot \sum_i B_i(P_j) \tag{14}$$

Figure 8A:
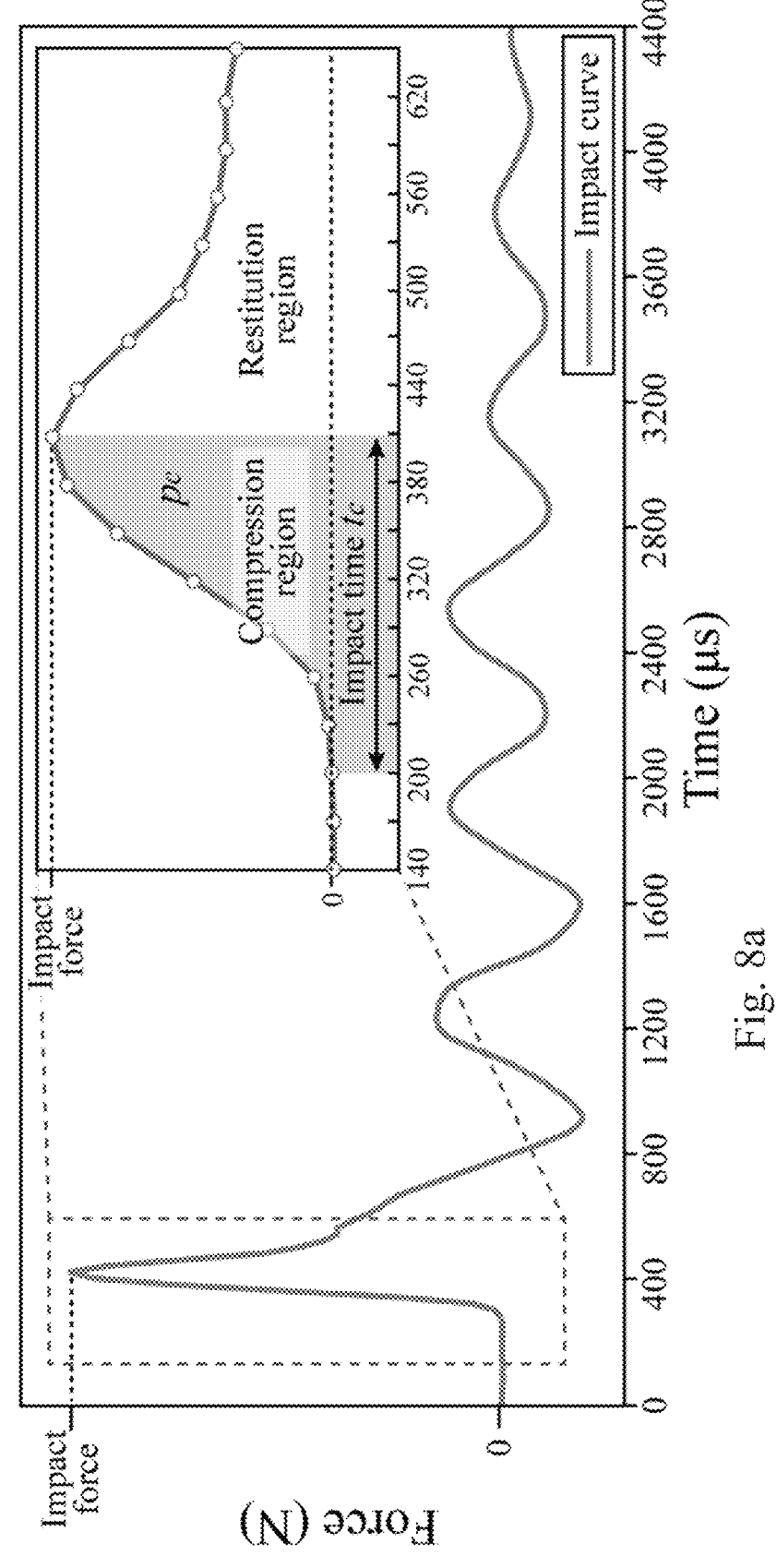
FIG. 8a shows a representative measured impact force profile from the experimental setup of FIG. 7.

As PM1 hits the end at the right-hand side, the impact force F(t) is calculated based on the momentum theorem:

$$p_c = -\overline{m}v_{P_2} = \int_0^{t_e} F(t)dt \tag{15}$$

where $p_c$ is the momentum for compression and $t_c$ is the impact time. Considering a very small $t_c$ as measured during experiment, it is assumed that the impact force F(t) is independent of time and is denoted as F. The force acts on the inner wall and transfers to the robot structure, partially lost as the impact is not perfectly elastic. The loss of kinetic energy is calculated as [31]:

$$\Delta E = \frac{1}{2}\overline{m}v_{P_2}^2\left(1 - e_*^2\right) \tag{16}$$

where $e_*$ is the kinematic coefficient of restitution. Considering the collision without viscoelastic dissipation, ex is calculated as:

$$e_* = \frac{p_f - p_c}{p_c} \tag{17}$$

where $p_f$ is the terminal impulse for restitution in the robot body illustrated in FIG. 8a. Through the free drop experiment as will be explained below, the restitution coefficient is measured as $e_*=0.35\pm0.04$. Combining (13) to (17), one can obtain the impact force F of the triple-magnet system applied to the environment.

Figure 6A:
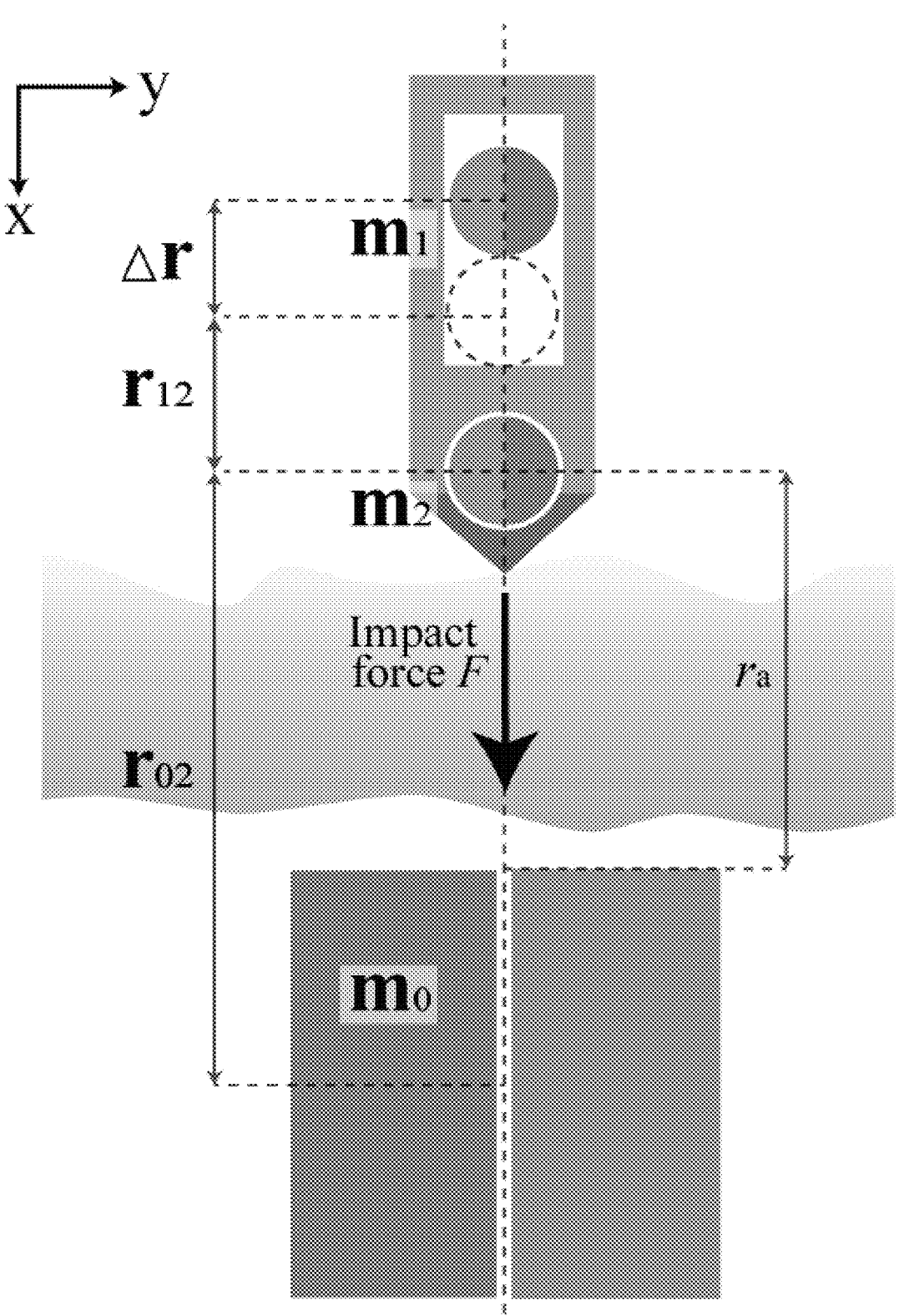
FIG. 6a illustrates parameters optimization for the triple-magnet system of the magnetic impact needle robot of FIG. 3, including definitions of the relevant parameters of the triple-magnet system in real-world applications.

Next, the optimization of the magnetic robot will be discussed. The aim is to maximize impact force F for the triple-magnet system. According to the mathematical model analyzed above, the impact force F is tuned with parameters $(m_0, m_1, m_2, r_{12}, r_{02})$, as illustrated in FIG. 6a. In FIG. 6a, a specific available operation distance $r_a$ is marked out.

Figure 6B:
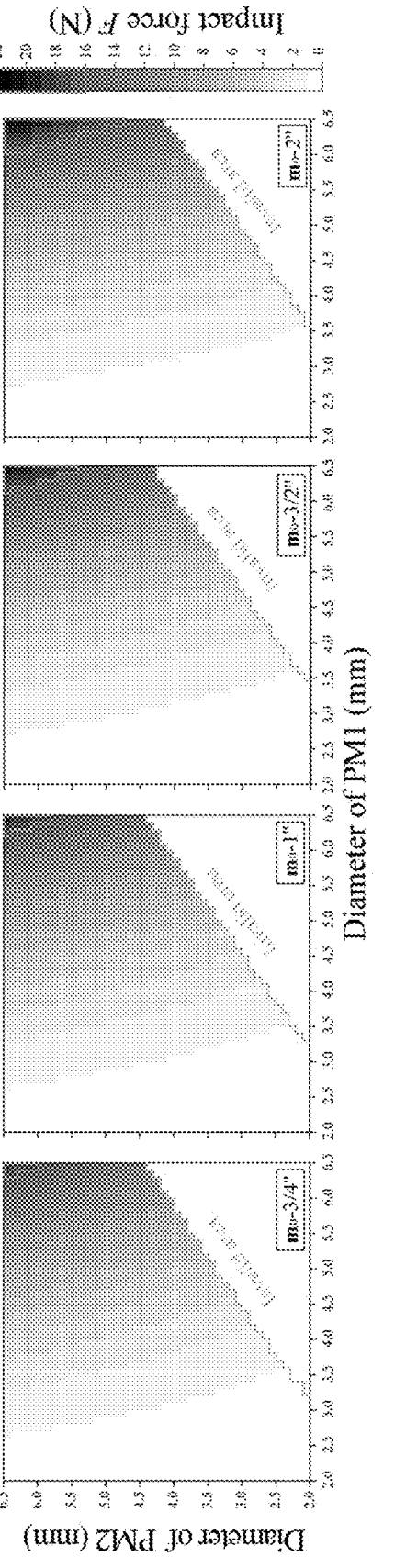

A uniform magnetization M of commercially available NdFeB magnets is considered, where PM1 and PM2 are N42-graded (K&J Inc.) spherical magnets, and PM0 is an N52-graded (X-Mag Inc.) cubic magnet. The magnetic moments are calculated as follows:

$$m_i = M_i V_i \tag{18}$$

where $M_i$ is the magnetization, varying with the magnetic grades, and $V_i$ is the volume of the magnetic components. Based on the model presented above, the impact forces with varying diameters of PM1 and PM2 are presented in FIG. 6b. In FIG. 6b, four groups of PM0 with different sidelength values are evaluated. Invalid areas are marked, while impact forces exceeding 16.0 N are highlighted with cascading lines at the upper right corner of each sub-image. $r_{12}=8.4$ mm, distance ratio $\alpha$, is the mean value of the upper and lower limits calculated from (8) and (11). Both diameters of PM1 and PM2, ranging from 2.0 mm to 6.5 mm, are simulated under the actuation of PM0 with diameters of $\frac{3}{4}$ inch, 1 inch, $\frac{3}{2}$ inches, and 2 inches. It is demonstrated that larger diameters in PM1 and PM2 generate a larger impact force, and the effect of the diameter change in PM1 is more significant than that in PM2. In addition, a triangular "Invalid area" with zero impact force is identified, where the PM2 cannot escape from the magnetic chaining state as PM0 rotates. Interestingly, increasing the magnetic moment in PM0 with a larger volume only slightly increases the impact force, and reduces the invalid area of zero impact force. The cubic magnets PM0 produce a similar magnetic gradient at their corresponding available distance range regardless of their volume, resulting in a similar impact force output. Based on the results from FIG. 4(b), we choose a diameter of 4.76 mm (³⁄₁₆ inch) for both PM1 and PM2, and a $r_{12}$=8.4 mm to minimize the angle difference and restrain the size of MINRob.

TABLE I

ACTUATING DISTANCE $r_{02}$
FOR PM0 WITH DIFFERENT SIDELENGTH

| Sidelength | Magnetic moment $m_0$ | Minimum $r_{02}$ | Maximum $r_{02}$ |
|---|---|---|---|
| ¾ inch | 8.0596 Am² | 21.44 mm | 31.57 mm |
| 1 inch | 19.1042 Am² | 28.63 mm | 42.10 mm |
| ½ inches | 64.4767 Am² | 41.79 mm | 63.14 mm |
| 2 inches | 140.3170 Am² | 53.87 mm | 84.19 mm |

TABLE II

SPECIFICATIONS OF THE TRIPLE-MAGNET SYSTEM

| Symbol | Description | Value |
|---|---|---|
| $m_0$ | Magnetic moment of the actuating cube | 140.3170 Am² |
| $m_1$ | Magnetic moment of the active sphere | 0.0506 Am² |
| $m_2$ | Magnetic moment of the passive sphere | 0.0506 Am² |
| $r_{12}$ | Distance between PM1 and PM2 | 8.4 mm |
| $r_{02}$ | Distance between PM0 and PM2 | 75.6 mm |
| $\alpha_r$ | Distance ratio of $r_{02}$ over $r_{12}$ | 9:1 |
| $l_{chamber}$ | Length of the inner chamber of MINRob | 8.0 mm |
| $l_{robot}$ | Total axial length of MINRob | 17.5 mm |
| $d_{robot}$ | Diameter of MINRob | 5.6 mm |
| $l_{needle}$ | Length of the needle | 7.0 mm |
| $d_{needle}$ | Diameter of the needle | 0.5 mm |

Nonetheless, the magnetic moment in PM0 significantly affects the actuating distance. The distance ratios $\alpha_r$ are calculated through (8) and (11). The corresponding actuating distance $r_{02}$ follows:

$$\left( \left( \frac{m_0}{m_2} \right)^{\frac{1}{4}} - 1 \right) r_{12} \leq r_{02} \leq \left( \frac{m_0}{3m_1} \right)^{\frac{1}{3}} r_{12} \tag{19}$$

Figure 6C:
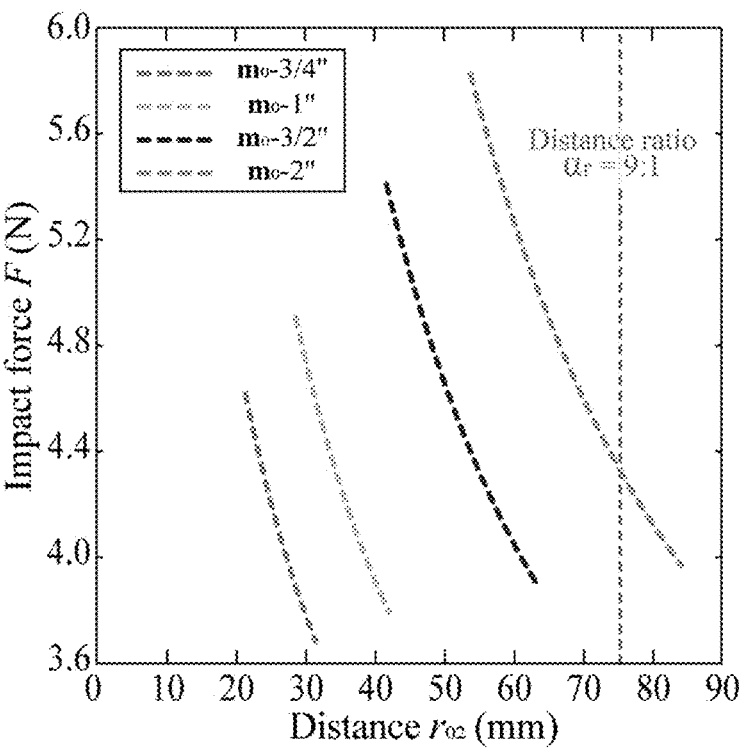
Figure 6D:
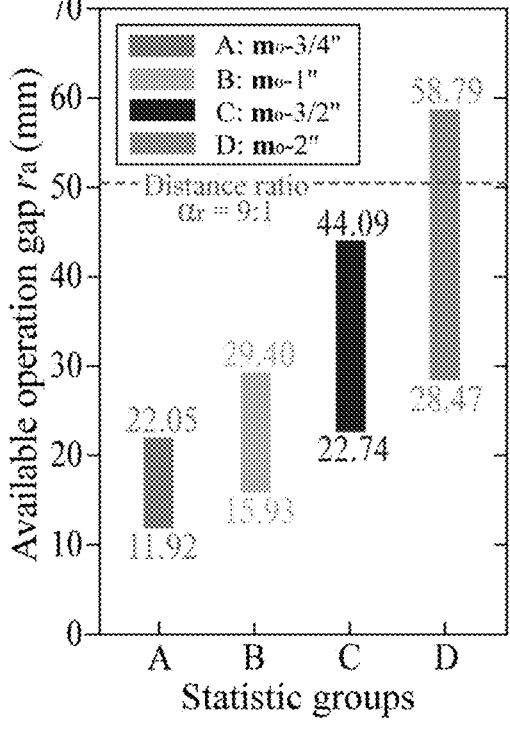

The distance ranges of four groups of PM0 are listed in Table I, and the corresponding impact force values are plotted to the left of FIG. 6c. The transition between the chaining state and the pre-bouncing state determines the range of the actuating distance $r_{02}$. The impact force increases with the increase of $m_0$, and decreases rapidly with the increase of $r_{02}$.

In biomedical applications, the available operation ranges need to be larger than the thickness of the wall of specific skin and organs in human bodies. Considering the volume of PM0, we define the available operation gap $r_a$, which is the gap between MINRob and actuating magnets, marked in the FIG. 6a. Thus, the available operation distance between the robot and the surface of the actuating magnet is plotted on the right-hand-side of FIG. 6c. In our experiments, an N52-graded magnetic cube with a sidelength of 2 inches is chosen to ensure the proposed system is applicable for potential in vivo wireless actuation in the future. The corresponding maximum available distance $r_a$ is 58.79 mm, sufficient for operations in abdominal organs [32].

Based on the results of optimization, the fundamental parameters of MINRob and the triple-magnet system are determined and listed in Table II. The values of the magnetic moment are measured by a Gaussmeter (MAGSYS HGM09s) and calculated in MATLAB via (2). MINRob has a total length of 17.5 mm and a diameter of 5.6 mm. Both spherical magnets PM1 and PM2 are sealed inside the external shell made of PLA as introduced in Section II. Both the inner spherical and cylindrical chambers have a slightly larger diameter (5.1 mm) than the diameter of PM2 and PM1, resulting in free rotation. Meanwhile, the cylindrical chamber with a length of 8 mm allows PM1 to translate reciprocally. We fix a $r_{12}$=8.4 mm and a $\alpha_r$=9:1 to control the total length of MINRob and ensure safety in experiments. The N42-graded NdFeB spherical magnet with a diameter of ³⁄₁₆ inch (K&J Inc.) is chosen for both PM1 and PM2.

A free drop experiment is further conducted to estimate ex in the impact process as introduced previously. In this experiment, the same spherical magnet PM1 as used in the proposed robot is released to the substrate with the same material (PLA) as the 3D-printed external shell. By calculating the ratio of free drop height and bounce-off height, $e_*$ is measured as 0.35±0.04.

Next, characterization of the triple-magnet system will be discussed. The aim here is to measure the force generated by the proposed triple-magnet system and collect real-time images simultaneously. In the experimental setups, it is infeasible to directly place the force sensor between the actuating magnet and the robot. The force sensor will collide with the rotating magnet, and the strong time-varying magnetic field induces an undesired perturbation in measurements. To avoid the aforementioned issues, there is designed a customized experimental setup to measure the impact force indirectly, as shown in FIG. 7. A brushless motor 144 is coupled to a third magnet 120 of the magnet impact device so that the third magnet 120 may be driven for rotation and function as an actuating magnet. Separate from the third magnet 120 is a millirobot containing two spherical magnets which are a first magnet 122 and a second magnet 124 that are received within a casing 126. The casing 126 which is made of plastic allowing the structure to hit an impact plate 146 to mimic the impact process of MINRob in FIGS. 1-2. Again in this embodiment the third magnet 120 is denoted as PM0, the first magnet 122 as PM1, and the second magnet 124 as PM2. The millirobot is movably located within an impact plate 146 that has a rectangular shape, and within the impact plate 146 there is also a force sensor 148 installed which is adapted to be impinged by the millirobot to measure an impact force F exerted by the millirobot. The configuration of the first magnet 122, the second magnet 124 and the third magnet 120 are similar to that shown in FIGS. 1-2, and will not be described in detail again. The impact experiments have the same parameters as the triple-magnet system, as defined in Table II.

The impact plate 146 is 3D printed via carbon fiber reinforced ABS and is placed inside a groove with WD-40 lubricant to reduce friction. The sensor 148 which is a piezoelectric force sensor (DYTRAN 1051V1, 10 LbF) with a non-magnetic impact cap and a data acquisition module (DEWSOFT IOLITEi-1×ACC, 50 kHz) is placed sufficiently far from the third magnet 120. The impact force from the robot is transmitted to the force sensor 148 via the impact plate 146, which is lightweight with ideal impact property

[33], [34]. Two spherical magnets, PM1 and PM2 are enclosed in a structure similar to MINRob.

Figure 8B:
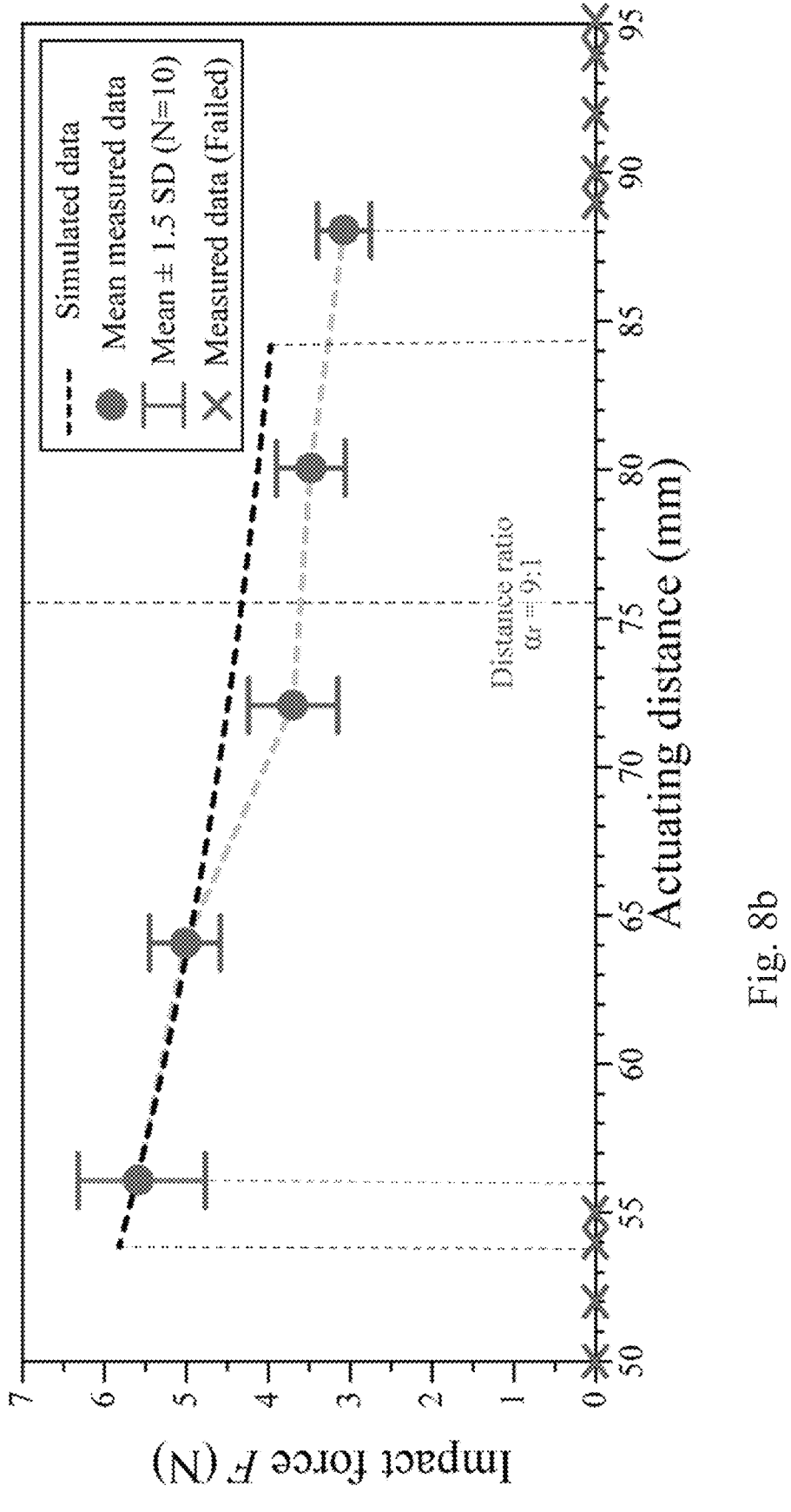
FIG. 8b shows impact force with varying actuating distances, including measured data presented and compared with simulated data, for the experimental setup of FIG. 7.
Figure 8C:
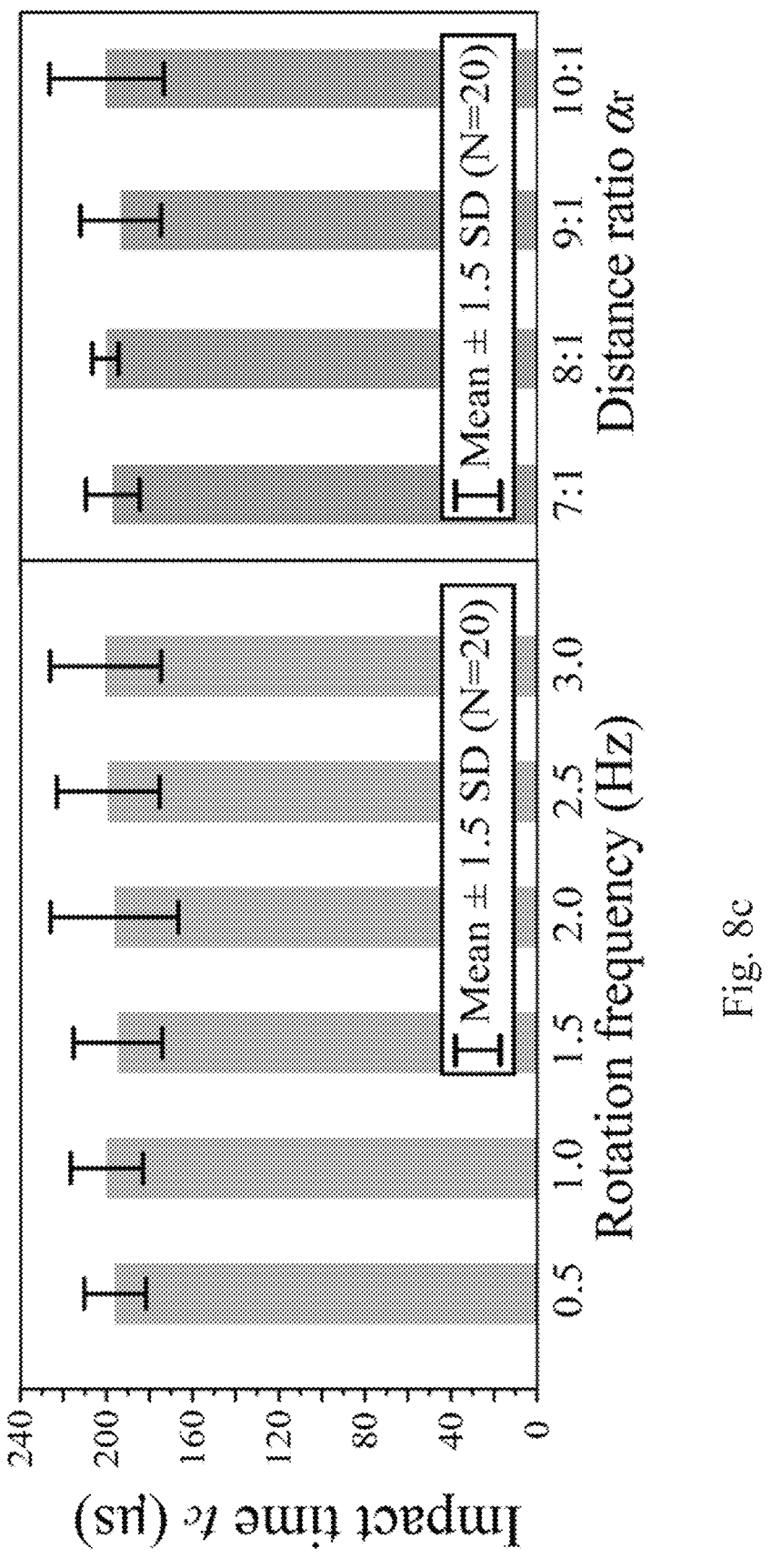
FIG. 8*c* illustrates a graph showing the impact time $t_c$ varies with the rotation frequency of the motor, as well as the Impact time $t_c$ varies with distance ratio $\alpha_r$, for the experimental setup of FIG. 7.

A representative impact force curve is illustrated in FIG. 8$a$. A one-time impact curve is composed of the compression region and restitution region. The compression region is marked with shades, and is considered the impact region, while the differences of X and Y coordinates are time t and impact force F, respectively. To measure the impact force at different actuating distances, an external support is further applied to fix the PM1 at the distal end first, holding a bouncing-off state before releasing PM1 as PM0 rotates to the ideal configuration, as described in FIG. 5$e$. The results are presented in FIG. 8$b$, where the impact force output decreases as the actuating distance increases. The force values and available actuating distance ranges are presented and compared with the simulated data. The cross stands for the actuating distance, where the triple-magnet system is not able to operate, i.e., PM1 cannot bounce off. Error bar represents ±1.5 standard deviations (SD), sample size (N)=10. Meanwhile, the available actuating distance $r_{02}$ ∈ [56, 88] (mm) is experimentally demonstrated, where PM1 bounces off with the rotation of PM0. The impact forces in experiments are comparable to the model predictions in FIG. 6$c$, and an actuating distance $r_{02}$∈[53.87, 84.19] (mm) predicted by Table I also matches well with experiments.

The rotation frequencies of the actuating magnet (PM0) also affect the impact process. Its effect is investigated by measuring the evolution of impact force over time in experiments. As presented in FIG. 8$a$, the collision between the active spherical magnet PM1 and the robot body is divided into the compression and restitution phases. In the compression phase, the kinetic energy of PM1 is transformed into the elastic energy of the contact surface and dissipation energy. Afterward, the elastic energy is released during the restitution phase. Herein, the impact time $t_c$ is defined as the duration of the compression phase, while impact force F is the peak force value [31]. Experiments showed that the impact time $t_c$ is not significantly affected by rotation frequency (FIG. 8$c$). In FIG. 8$c$, the left graph shows impact time $t_c$ varies with the rotation frequency of the motor. Distance ratio $\alpha_r$=9:1. The right graph shows impact time $t_c$ varies with distance ratio $\alpha_r$. Rotation frequency=0.5 Hz. Error bar represents ±1.5 SD, sample size (N)=20. In addition, an approximately constant impact time $t_c$=200 μs is observed in the triple-magnet system for different distance ratios $\alpha_r$. It is noted that an impact time $t_c$=400 μs has been reported in impact between a magnetic part and a glass mica ceramic contact surface [22].

Although different rotation frequencies result in a constant impact time $t_c$=200 μs, they still affect the impact force. As illustrated in FIG. 9$a$, F increases with increasing rotation frequency from 0.25 Hz to 3.0 Hz. PM1 is static for a certain period at the proximal end after each impact. Thus the dynamic effect (e.g., kinetic energy accumulation after each impact) from the continuously rotating magnetic field is negligible. During the impact experiment, PM1 has already hit back before PM0 rotates to an ideal configuration where $\theta_0$=−π as illustrated in FIG. 5$e$. Since both the bouncing-off and hitting-back time of PM1 are much shorter than the period of the rotation of the actuating magnet. Thus, it is derived that:

During the impact experiment, PM1 has already hit back before PM0 rotates to an ideal configuration where $\theta_0$=−π as illustrated in FIG. 5$e$. Since both the bouncing-off and hitting-back time of PM1 are much shorter than the period of the rotation of the actuating magnet. Thus, one will have:

$$|\theta^*| < \pi \tag{20}$$

where $$\theta_0^*$$

is the rotating angle of PM0 at the instant PM1 hits back. The hitting-back angle $$\theta_0^*$$

at different rotation frequencies of the motor is further evaluated, as shown in FIG. 9$b$. A similar trend is observed in FIG. 9$b$ matching with data from FIG. 9$a$. The angle data are obtained via a high-speed optical camera, and the detailed information is introduced in the following subsection. As the rotation frequency rises from 0.25 Hz to 3.0 Hz, $$|\theta_0^*|$$

increases from 96.54° to 105.86°. The results implied that a higher rotation frequency allows the PM0 to rotate for a larger $$|\theta_0^*|,$$

getting closer to the ideal configuration of |θ0*|=π in FIG. 5$e$, and thus the increment of impact force output is observed.

In summary, it is experimentally suggested that the rotation frequency of the actuating magnets affects the impact forces of the triple-magnet system. Instead of changing the impact time $t_c$, it changes the hitting-back angle $$\theta_0^*,$$

and the subsequent impact process. Although the impact force increases with the rotation frequency, it is suggested that by manipulating such a large permanent magnet with a robotic arm, the rotation frequency should not exceed 0.5 Hz [11], [12]. Thus, 0.5 Hz is chosen as the standard rotation frequency for the actuating magnets to balance force and safety. Further tuning the angle $$\theta_0^*$$

during the hitting-back process to achieve better performance is beyond the scope of the current study.

Additionally, the hitting-back angle $$\theta_0^*$$

is estimated based on the above mathematical model. For an ideal state presented in FIG. 5e, both attractive forces $$F^X_{01max}$$

and $$F^X_{21max}$$

exerted on PM1 contribute to the acceleration during the hitting-back process. The components in the X-axis of these attractive forces are maximized because all magnetic dipole moments of PM0, PM1, and PM2 align with each other along the X-axis.

If PM1 hits back as described in (20), the attractive force from PM0 has a Y component, resulting in an undesired swing, and the rest of the attractive force in the X-axis is calculated as:

$$F^X_{01} = F_{01max}\cos\theta^*_0 \qquad (21)$$

Hence, as $$\theta^* \to -\pi,\ F^X_{01}$$

is maximized. This alignment for PM0 in the X component contributes to a larger magnetic potential energy of PM1 as described in (13) due to the potential energy induced simultaneously by PM0 and PM2:

$$U_{P_j} = -m_1 \cdot \sum_{i=0,2} B_i(P_j) = -m_1 \cdot (B_0(P_j) + B_2(P_j)) \qquad (22)$$

where $B_0(P_j)$ and $B_2(P_j)$ is the magnetic flux density at point $P_j$ generated by PM0 and PM2, respectively. When $\theta^*=-\pi$, $|m_1 \cdot B_2(P_2)|$ is maximized, and thus a maximum impact force F is achieved by (13), (14), and (15).

In the embodiment shown in FIG. 7, the influence of various $$\theta^*_0$$

of to the impact force F for the magnetic robot is experimentally investigated through the setup in FIG. 7. In the initial configuration, the active spherical magnet PM1 is fixed by the external support to its bouncing-off state. When the actuating permanent magnet PM0 rotates to a specific angle $$\theta^*_0,$$

the external support is removed, and the impact force values are recorded. The experimental data is presented in FIG. 9c and compared with the simulated data measured by (21). In FIG. 9c, error bar represents ±1.5 SD, sample size (N)=20. Here, −

$$-\theta^*_0$$

∈ [90°, 110°] is evaluated, which is the achievable range of the present peripheral via tuning the rotation frequency. It is experimentally proved that a larger hitting-back angle |

$$|\theta^*_0|$$

of the triple-magnet system generates a larger impact force.

To verify the applicability of the proposed triple-magnet system, the same experimental setup in FIG. 7 is employed using a high-speed optical camera 140 (for example, MotionBLITZ mini2 from Mikrotron GmbH) to obtain real-time imaging illustrating the position and orientation of each magnetic component in the triple-magnet system. LED light panels 142 are also installed to provide illuminations to the field of vision of the camera 140. A metal spray paint is applied to the south pole of PM1 and PM2 with black dyeing, and thus the direction of the magnetic moment is visualized during the rotation. The images are obtained at a frame rate of 1000 fps and rotation frequencies of PM0 range from 0.25 to 3.0 Hz.

Representative curves for the angle variations of PM1 and PM2 in a complete rotation period at 0.5 Hz are presented in FIG. 10. The data are obtained by the high-speed camera in a complete rotation period at a rotation frequency of 0.5 Hz. The mean angle values are presented in the figure with a sample size of 5, while specific angles are marked out. Snapshots of the specific transitional states are listed together with corresponding FEA results illustrating the magnetic flux density distribution. Sub-graph I in FIG. 10 shows transitional states between magnetic chaining state and pre-bouncing state. Sub-graph II shows transitional states between pre-bouncing state and bouncing-off state. Sub-graph III shows transitional states between bouncing-off state and hitting-back state. Sub-graph IV shows the ending moment of the hitting-back state. The angle data are presented as the mean measured value with a sample size of 5. The real-time rotation angles of PM1 and PM2 are denoted as $\theta_1$ and $\theta_2$, respectively. During the magnetic chaining and pre-bouncing state, the curves for both $\theta_1$ and $\theta_2$ are the same. The peak angle difference is $|\theta_1-\theta_2|=2.31°$, verifying the assumptions of $\theta1=\theta2$ in the mathematical model presented above. As PM1 starts to bounce off and further hit back, the angle difference increases as the local interactions between PM1 and PM2 weaken. In the bouncing-off and hitting-back state, the impact process is measured with the energy in (14) and (15), where a large angle difference is observed. Eventually, $\theta_1$ and $\theta_2$ approach each other and increase simultaneously to $\pi$ in an aligning manner, as illustrated in FIG. 10.

The proposed five states (i.e., aligning state, magnetic chaining state, pre-bouncing state, bouncing-off state, and hitting-back state) are observed in experiments. They are illustrated in FIG. 10 with different background grayscales. Specific critical angles of transitions between states are marked out, for which the real-time images illustrating the position and orientation of PM1 and PM2 are presented in the figure. For a rotation frequency of 0.5 Hz, the duration of 21 ms, 10 ms, and 65 ms are recorded for the pre-bouncing state, bouncing-off state, and hitting-back state, respectively.

Correspondingly, an FEA is demonstrated in COMSOL Multiphysics 5.5 for magnetic flux density distribution of the triple-magnet system in a complete rotation period. A specific configuration $[00, 01, 02]=[-67.89°, 31.87°, 32.71°]$ is illustrated for magnetic chaining state. The region of interest (ROI) between PM1 and PM2 presents a strong connection with a high magnetic flux density. The magnetic chaining state is reached in a con-figuration of $[\theta_{m\_0}, \theta_{m\_1}, \theta_{m\_2}]=[-84.90°, 56.05°, 53.74°]$, where the magnetic flux density of the ROI decreases as $|\theta_0|$ increases. As a critical configuration $[\theta_{b\_0}, \theta_{b\_1}, \theta_{b\_2}]=[-87.07°, 67.69°, 64.76°]$ is accomplished during the pre-bouncing state, a low mag-netic: flux density of the ROI results in the magnetic repulsive force between PM1 and PM2, leading to the bouncing-off in PM1. A maximum bouncing-off distance $\Delta_{max}$ is observed during the bouncing-off state in a configu-ration $[00, 01, 02]=[-88.52°, 87.14°, 83.12°]$. Eventually, PM1 hits back in a configuration $$[\theta_0^*, \theta_{h\_1}, \theta_{h\_2}] = [-98.16°, 132.85°, 114.39°].$$

Next, the locomotion and functionality of a teleoperation robotic system according to another embodiment of the invention are investigated. The system is a triple-magnet teleoperation robotic system for creating a remotely con-trollable and programmable magnetic field, as illustrated in FIG. 11. The system includes a workbench 250, a MINRob 254, an actuating permanent magnet 220, a brushless direct current (DC) motor 244, a 7 DOFs robotic arm 230, an optical camera 240, and a personal computer (PC) 264. The customized workbench 250 is composed of a rectangular 2D plane and a hollow tube with a multi-layer film 256 attached to its end is fabricated. The locomotion and penetration performance of the MINRob 254 is demonstrated in the 2D plane and the tube, respectively. The teleoperation robotic system is controlled by a keyboard 264 and a mouse 266 of the PC 264.

A commercially available cubic permanent magnet (e.g., N52-graded NdFeB, X-Mag Inc.) with a sidelength of 2 inches is chosen as the actuating magnet PM0 (designated by the part number 220 in FIG. 11). Its rotation is controlled via the brushless DC motor 244 by tuning its rotation frequency and orientation. The brushless DC motor 244 has a maximum no-load rotation speed of 307 rpm and a rated torque of around 4.63 Nm. PM0 is concentrically connected with the rotation axis of the motor 244 via a 3D-printed mold. Together with the motor 244, the actuating magnet 220 is attached to the tip of a 7 DOFs robotic arm 230 (e.g., ROKAE xMate ER7 Pro) using an aluminum frame and a 3D-printed base. By adjusting the parameters of each joint of the robotic arm 230, the orientation and position of PM0 can be accurately controlled. Due to a limit of the maximum rotation angle of each joint in the robotic arm 230, the rotation of the actuating magnet 220 is mainly controlled by the brushless DC motor 244. The state, direction, and rotation frequency can be programmed in an Arduino circuit plate 258 and controlled by a PC. The Arduino circuit plate 258 is connected to a motor driver board 260 which in turn is connected to a power supply 262. Here, the actuating permanent magnet PM0 and the motor 244 are shown in FIG. 11, and the orientation of the PM0 is fixed. By controlling the translation of PM0 via the robotic arm 230

(approximately 12 cm beneath the workbench 250), the MINRob 254 will navigate on the planar surface.

Furthermore, an optical camera 240 and Open Source Computer Vision (OpenCV) library (not shown) are employed to record the outline of the MINRob 254 and obtain its position and orientation. The optical camera 240 is supported on a support frame 252. By connecting to the PC, a customized C++ program controls the position and orien-tation of the MINRob 254 remotely. The user can use the mouse 246 to provide a targeted position $$P_t^c$$

$\in R^{2 \times 1}$ in the frame of the camera $O^c(x_c, y_c)$ by clicking the right button in the operation interface, where the real-time images are provided by the camera 240. Afterward, $$P_t^c$$

is transferred into position $$P_t^w$$

$\in R^{2 \times 1}$ in the frame of the workbench 250 $O^w(x_w, y_w)$ by translating the digital pixel from the user interface to the real-world dimension of the workbench 250. Finally, posi-tion $$P_t^w$$

is transferred into $$P_t^r$$

$\in R^{2 \times 1}$ in the frame of the robotic arm 230 $O^r(x_r, y_r)$ based on the relative position between the workbench 250 and the end tip of the robotic arm 230. The robotic arm locates the PM0 to the targeted point $$P_t^r,$$

and the MINRob 254 is navigated to the targeted position $$P_t^w$$

in the workbench 250.

A position judgment and collaboration procedure is intro-duced to evaluate the translation's precision. The coordi-nates of both robot and the targeted point are displayed during the translation. If the mismatch of the targeted position and terminal robot position is smaller than one body length of the MINRob 254, the moving is considered a successful process and displays the text: "Move finish!".

Otherwise, a collaboration procedure is implemented, where PM0 moves vertically away from the workbench 250 and returns to the initial position to restart the movement.

To adjust the orientation of the MINRob 254, the robotic arm 230 rotates the PM0 to exert a magnetic torque, forcing the MINRob 254 to align with its magnetic moment through rotation. By pressing the "←" ("→") button on the keyboard 244, PM0 rotates counterclockwise (clockwise) along the Z-axis, resulting in the same rotation of the MINRob 254, and enables the orientation control of MINRob 254.

The demonstration of planar locomotion is presented in FIG. 12a. By clicking via the mouse 246, the MINRob 254 is able to reach the targeted position, while a controllable rotation is accomplished by pressing the keyboard 244. The command interface shows the real-time coordinate of the robot's position while displaying the coordinate of the targeted position after each click via the mouse 246. The MINRob 254 successfully moves to the targeted positions in the rectangular plane with a distance mismatch less than one body length. The trajectory of the MINRob 254 is shown with the dotted line. Afterward, the MINRob 254 is rotated to be aligned with the axial direction of the hollow tube by pressing the "←" and "→" buttons on the keyboard 244. Ultimately, the MINRob 254 is driven into the hollow tube after a total time of 69 s.

In summary, the planar locomotions of the MINRob 254, including the translation and rotation performance, are demonstrated with a teleoperation robotic system. Such a system accomplishes the remotely programmable and precise manipulation of the MINRob 254, indicating a potential application to be integrated with the advanced robot-assisted operation system. In addition, a 3D rolling locomotion is achieved by rotating PM0 in the lateral plane, as illustrated in FIG. 12d. In FIG. 12d, a forth and back rolling is achieved under the rotation of the actuating permanent magnet PM0 in the lateral direction.

The performance of the triple-magnet system as shown in FIG. 11 to generate a larger force is evaluated by the penetration experiment. The hollow tube (not shown) in the workbench 250 has an inner diameter of 6 mm, slightly larger than the MINRob 254. A multi-layer laboratory film 256 (Parafilm M), which is composed of a bend of waxes and polyolefins, is attached at the distal end. After the MINRob 254 is navigated into the hollow tube, the actuating permanent magnet PM0 further pulls the MINRob 254 to the distal end. Afterward, PM0 is located to a targeted position by the robotic arm and starts to rotate at a safe frequency of 0.5 Hz.

As shown in FIG. 12b, the triple-magnet system actuates the repeatable impact due to the rotation of PM0, which generate a continuous force output. The clinical needle (not shown in FIG. 11) attached to the MINRob tip can puncture five layers of film within 30 s. The bouncing-off and hitting-back procedures of the PM1 are observed, while an obvious puncture is observed from the needle tip after each impact, verifying the applicability of the triple-magnet system in the real device. The corresponding control group is shown in FIG. 12c, where PM0 is placed in the same position while the magnetic dipole moment is aligned with the axial direction of the MINRob 254 to induce a pure magnetic attractive force. It is observed that MINRob 254 is not able to puncture the multi-layer film in such a configuration for more than 30 min, indicating the pure magnetic attractive force is insufficient to penetrate the film at the same condition.

To quantitatively evaluate the penetration performance, a digital force gauge (HANDPI, 10 N, 0.01%) is employed to measure the puncture force and the pull-out force of the MINRob, as shown in FIG. 13. The multi-layer film is fixed on a jig, and thus the puncture force and the pull-out force are measured during a complete insertion and extraction process, respectively. The robot body is encapsulated by a 3D-printed casing connected to the force gauge, while the force gauge is fixed on a spiral test rack which can provide a precise and controllable displacement in the vertical direction. By providing a similar approaching speed for the MINRob as measured from the experiment, the force curve is measured for both the penetration and pull-out process. Representative curves for puncture and pull-out forces with increasing penetration depth are illustrated in FIG. 14a. In FIG. 14a, the peak force values represent the mean value±1.5 SD, with the sample size being 24. A peak puncture force of −560.63±17.72 mN is measured, while a peak pull-out force is 453.56±14.21 mN. It is noted that the pure magnetic attractive force in FIG. 12c is measured to be 171.13 mN based on (3). The corresponding impact force for the triple-magnet system with a 0.5 Hz rotation frequency is measured to be 1.81 N, indicating a 10-fold increase. Thus, the triple-magnet system is able to provide a significantly larger outputting force compared with a pure magnetic pulling force. It is capable of being applied for tissue penetration while providing substantial anchoring.

In the previous sections, the reliability of the triple-magnet system is verified by mathematical modeling and experimental demonstrations. Based on this, the MINRob is designed. Under an externally rotating permanent magnet, the MINRob is able to achieve reversible and continuous 1D collision in 3D space by controlling the position and orientation of the triple-magnet system. In a similar manner as described in the preceding work [22], the 1D impact motion is able to be extended to a 3D space providing flexible and controllable locomotions.

TABLE III

SPECIFICATIONS OF THE
PARAMETERS IN FIG. 14B

| Symbol | Description | Value [Ref.] |
|---|---|---|
| $F_1$ | Puncture force for mouse brain | 2.50 mN [35] |
| $F_2$ | Puncture force for human corner | 282 mN [36] |
| $F_3$ | Puncture force for piglet skin | 0.54 N [37] |
| $F_4$ | Puncture force for porcine tissue | 1.28 N [38] |
| $F_5$ | Pancture force for piglet skin (blunted needle) | 3.54 N [37] |

TABLE IV

A COMPARISON OF THE OUTPUTTING FORCE
OF MINIATURE MAGNETIC ROBOTS

| Ref. | Characteristic length | Repeatable operation | Force output |
|---|---|---|---|
| [18] | 3.2 mm | No | 0.95 N |
| [17] | 10.8 mm | No | ~2 N |
| [39] | 15.0 mm | Yes | 35 mN |
| [40] | 21.0 mm | Yes | 6 mN |
| [41] | 22.0 mm | Yes | 0.60 N |
| [22] | 35.4 mm | Yes | 0.41 N |
| [19] | 100 mm | No | ~0.59 N |
| This work | 17.5 mm | Yes | 2.92 N |

The proposed MINRob is able to provide continuous outputting forces ranging from 1.17 N to 2.92 N under various rotation frequencies (from 0.25 Hz to 3.0 Hz). These values are illustrated in FIG. 14*b* while comparing to specific force thresholds in biomedical applications, and the corresponding force parameters are listed in Table III. Compared to the conventional magnetic miniature robots driven by attractive magnetic force (171.13 mN) with the same characteristic length, our triple-magnet system provides a force output with a tenfold increase. For a rotation frequency of 0.5 Hz, an impact force of 1.81 N is accomplished, which is sufficient for penetrating the mouse brain, human cornea, piglet skin, and porcine tissue.

Furthermore, a comparison of a magnet impact device according to an embodiment of the invention (denoted by "This work" in Table IV) with the current miniature magnetic robots with a similar characteristic length or working principle is presented in Table IV. Previous small-scale robots cannot simultaneously accomplish a sufficient force output and continuous operation. The triple-magnet system introduced here achieves a significantly large force output accompanied by a repeatable operation. In addition, its force output is adjustable by controlling the rotation frequency of PM0, for which we can constrain the force output of MINRob to protect the tissue from being penetrated in specific surgical situations.

One can see that in the exemplary embodiment described above, there is proposed a novel triple-magnet system, which enables a reversible and repeatable magnetic collision between two spherical magnets. The proposed mechanism is verified by mathematical modeling and experiments. To extend the application of the triple-magnet system, a miniature device MINRob, is introduced based on the magnetic impact to exert large force via a needle, integrating with a teleoperation system. Eventually, experimental demonstrations are presented to evaluate the locomotion and penetration performance of the MINRob. A comparison is provided between the output force and the achievable force range between our work and the current miniature magnetic robots, indicating the potential applications of the triple-magnet system in tissue penetration. The proposed MINRob and triple-magnet system demonstrate great potential to access deep tissue and conduct operations (e.g., tissue biopsy and drug delivery), inspiring the development of small-scale robots that are more applicable to the real-world biomedical workspace. It has demonstrated various locomotion patterns (including down-actuating, side-actuating, and front-actuating) that is applicable to specific medical applications (e.g., deep vein thrombosis, intestinal obstruction, and bladder cancer.). The proposed MINRob based on the triple-magnet system enables long-lasting anchoring, tumor cell biopsy, and targeted drug.

The exemplary embodiments are thus fully described. Although the description referred to particular embodiments, it will be clear to one skilled in the art that the invention may be practiced with variation of these specific details. Hence this invention should not be construed as limited to the embodiments set forth herein.

While the embodiments have been illustrated and described in detail in the drawings and foregoing description, the same is to be considered as illustrative and not restrictive in character, it being understood that only exemplary embodiments have been shown and described and do not limit the scope of the invention in any manner. It can be appreciated that any of the features described herein may be used with any embodiment. The illustrative embodiments are not exclusive of each other or of other embodiments not recited herein. Accordingly, the invention also provides embodiments that comprise combinations of one or more of the illustrative embodiments described above. Modifications and variations of the invention as herein set forth can be made without departing from the spirit and scope thereof, and, therefore, only such limitations should be imposed as are indicated by the appended claims.

What is claimed is:

1. A magnetic impact robot adapted to be deployed inside a human body, the magnetic impact robot comprising an impacting portion which comprises:
   a) a casing defining a first inner chamber and a second inner chamber;
   b) a first permanent magnet received within the first inner chamber; and
   c) a second permanent magnet received within the second inner chamber;
   wherein the impacting portion is adapted to perform a striking action along a linear direction as a result of the first permanent magnet colliding with the casing when the first permanent magnet and the second permanent magnet are actuated by a third permanent magnet that is external to the magnetic impact robot.

2. The magnetic impact robot of claim 1, wherein both of the first and second permanent magnets are spherical magnets.

3. The magnetic impact robot of claim 2, wherein the second permanent magnet and the first permanent magnet are adapted to rotate as a result of a rotation of the third permanent magnet, which further results in synchronized rotations of the first and second permanent magnets.

4. The magnetic impact robot of claim 3, wherein the impacting portion undergoes a complete striking cycle when the third permanent magnet undergoes an actuating cycle as it rotates.

5. The magnetic impact robot of claim 4, wherein during the complete striking cycle the first permanent magnet is repelled from the second permanent magnet and then bounces back, resulting in the striking action of the impacting portion.

6. The magnetic impact robot of claim 1, wherein the first permanent magnet is adapted to rotate and translate within the first inner chamber.

7. The magnetic impact robot of claim 1, wherein the first second permanent magnet is adapted to rotate only.

8. The magnetic impact robot of claim 1, wherein the first permanent magnet and the second permanent magnet are configured so as to not come into direct contact.

9. The magnetic impact robot of claim 1, wherein the first inner chamber is a cylindrical cavity, and the second inner chamber is a spherical cavity.

10. The magnetic impact robot of claim 1, further comprising a needle coupled to the impacting portion.

11. A magnet impact device, comprising:
   a) a magnetic impact robot according to claim 1; and
   b) a third permanent magnet external to the magnetic impact robot, which is adapted to actuate the magnetic impact robot.

12. The magnet impact device according to claim 11, wherein the third permanent magnet is adapted to rotate, resulting in synchronized rotations of the first and second permanent magnets.

13. The magnet impact device according to claim 11, wherein the actuating cycle of the third permanent magnet is 180° of rotation.

14. The magnet impact device of claim 11, wherein the third permanent magnet is a cubic permanent magnet.

15. A small-scale robotic system, comprising:

a) a magnet impact device according to claim 11;

b) a first robotic arm to which a camera or an ultrasonic probe is installed; and c) a second robotic arm to which the third permanent magnet of the magnet impact device and a motor are installed;

wherein the motor is coupled with the third permanent magnet and adapted to drive the third permanent magnet of the magnet impact device to rotate.

\* \* \* \* \*